(12) United States Patent
Bechtel et al.

(10) Patent No.: US 11,707,214 B2
(45) Date of Patent: *Jul. 25, 2023

(54) OXIMETRY PROBE WITH TISSUE DEPTH ANALYSIS

(71) Applicant: ViOptix, Inc., Newark, CA (US)

(72) Inventors: Kate LeeAnn Bechtel, Pleasant Hill, CA (US); Jennifer Elizabeth Keating, Campbell, CA (US); Scott Coleridge, Belle Mead, NJ (US)

(73) Assignee: ViOptix, Inc., Newark, CA (US)

( * ) Notice: Subject to any disclaimer, the term of this patent is extended or adjusted under 35 U.S.C. 154(b) by 293 days.

This patent is subject to a terminal disclaimer.

(21) Appl. No.: 17/094,701

(22) Filed: Nov. 10, 2020

(65) Prior Publication Data
US 2021/0052203 A1 Feb. 25, 2021

Related U.S. Application Data

(62) Division of application No. 15/493,111, filed on Apr. 20, 2017, now Pat. No. 10,827,957.
(Continued)

(51) Int. Cl.
*A61B 5/1455* (2006.01)
*A61B 5/107* (2006.01)
*A61B 5/00* (2006.01)

(52) U.S. Cl.
CPC ........ *A61B 5/14551* (2013.01); *A61B 5/1075* (2013.01); *A61B 5/14552* (2013.01); *A61B 5/6887* (2013.01); *A61B 5/7235* (2013.01); *A61B 2560/0214* (2013.01); *A61B 2560/0425* (2013.01); *A61B 2562/242* (2013.01); *A61B 2562/247* (2013.01)

(58) Field of Classification Search
CPC ............. A61B 5/1455; A61B 5/14551; A61B 5/14552; A61B 5/742; A61B 5/7235; A61B 5/1075; A61B 5/6887
See application file for complete search history.

(56) References Cited

U.S. PATENT DOCUMENTS 6,385,821 B1    5/2002  Modgil et al.
7,236,813 B2    6/2007  Parker
(Continued)

FOREIGN PATENT DOCUMENTS

EP    0102816 A2    3/1984
EP    1889569 B1    6/2014
(Continued)

OTHER PUBLICATIONS

International Search Report, PCT Application PCT/US2017/028699, dated Jul. 30, 2017, 9 pages.

*Primary Examiner* — Chu Chuan Liu
(74) *Attorney, Agent, or Firm* — Aka Chan LLP

(57) ABSTRACT

An oximeter probe includes a probe unit or a base unit and a probe tip where the probe tip has a number of sources and detectors that can be accessed individually or in differing combinations for measuring tissue oxygen saturation at different tissue depth in tissue. A processor of the oximeter probe controls a multiplexer that is coupled to the detectors for selectively collecting measurement information from the detectors via the multiplexer. The oximeter probe is user programmable via one or more input devices on the oximeter probe for selecting the particular sources and detectors to collect measurement information from by the processor.

13 Claims, 15 Drawing Sheets

Related U.S. Application Data

(60) Provisional application No. 62/363,562, filed on Jul. 18, 2016, provisional application No. 62/326,630, filed on Apr. 22, 2016, provisional application No. 62/326,673, filed on Apr. 22, 2016, provisional application No. 62/326,644, filed on Apr. 22, 2016, provisional application No. 62/325,919, filed on Apr. 21, 2016, provisional application No. 62/325,416, filed on Apr. 20, 2016, provisional application No. 62/325,403, filed on Apr. 20, 2016, provisional application No. 62/325,413, filed on Apr. 20, 2016.

(56) References Cited

U.S. PATENT DOCUMENTS

| | | |
|---|---|---|
| 8,233,955 B2 | 7/2012 | Al-Ali et al. |
| 8,938,279 B1 | 1/2015 | Heaton, II et al. |
| 2003/0009092 A1 | 1/2003 | Parker |
| 2004/0034294 A1 | 2/2004 | Kimball et al. |
| 2006/0053522 A1 | 3/2006 | Kimbell |
| 2007/0244377 A1 | 10/2007 | Cozad et al. |
| 2008/0319290 A1 | 12/2008 | Mao et al. |
| 2009/0253968 A1 | 10/2009 | Cho et al. |
| 2010/0005630 A1 | 1/2010 | Gitman et al. |
| 2010/0292549 A1 | 11/2010 | Shuler |
| 2010/0298728 A1 | 11/2010 | Addison et al. |
| 2011/0205535 A1 | 8/2011 | Soller et al. |
| 2011/0224518 A1 | 9/2011 | Tindi et al. |
| 2011/0276276 A1 | 11/2011 | Kashyap et al. |
| 2012/0289801 A1 | 11/2012 | Yamaguchi |
| 2013/0023743 A1 | 1/2013 | Al-Ali et al. |
| 2013/0317331 A1 | 11/2013 | Bechtel et al. |
| 2014/0046152 A1 | 2/2014 | Bechtel et al. |
| 2014/0180043 A1 | 6/2014 | Addison et al. |
| 2014/0288386 A1 | 9/2014 | Zand et al. |

FOREIGN PATENT DOCUMENTS

| | | |
|---|---|---|
| WO | 2009090665 A1 | 7/2009 |
| WO | 2010011763 | 1/2010 |
| WO | 2010042264 A1 | 4/2010 |
| WO | 2014026200 | 2/2014 |

OXIMETRY PROBE WITH TISSUE DEPTH ANALYSIS

CROSS-REFERENCE TO RELATED APPLICATIONS

This application is a divisional of U.S. patent application Ser. No. 15/493,111, filed Apr. 20, 2017, issued as U.S. Pat. No. 10,827,957 on Nov. 10, 2020, which claims the benefit of the following U.S. patent applications 62/325,403, 62/325,416, 62/325,413, filed Apr. 20, 2016, 62/325,919, filed Apr. 21, 2016, 62/326,630, 62/326,644, 62/326,673, filed Apr. 22, 2016, and 62/363,562, filed Jul. 18, 2016. These applications are incorporated by reference along with all other references cited in these applications.

BACKGROUND OF THE INVENTION

The present invention relates to oximeter probes, such as compact, handheld oximeter probes, that include sources and detectors having source-to-detector spacing that can be user selected for probing different tissue depth, that have sources that emit wavelengths of light (visible light, IR, or both) that can be user selected for probing different tissue depth, or both.

Oximeters are medical devices used to measure tissue oxygen saturation of tissue in humans and living things for various purposes. For example, oximeters are used for medical and diagnostic purposes in hospitals and other medical facilities (e.g., operating rooms for surgery, recovery room for patient monitoring, or ambulance or other mobile monitoring for, e.g., hypoxia); sports and athletic purposes at a sports arena (e.g., professional athlete monitoring); personal or at-home monitoring of individuals (e.g., local tissue health, regional tissue health, general health monitoring, or person training for a marathon); and veterinary purposes (e.g., animal monitoring).

In particular, assessing a patient's tissue oxygen saturation, at both the regional and local level, is important as it is an indicator of the state of the patient's local and regions tissue heath and can be an indicator of general health. Thus, oximeters are often used in clinical settings, such as during surgery and recovery, where it can be suspected that the patient's tissue oxygenation state is unstable. For example, during surgery, oximeters should be able to quickly deliver accurate tissue oxygen saturation measurements under a variety of non-ideal conditions. While existing oximeters have been sufficient for post-operative tissue monitoring where absolute accuracy is not critical and trending data alone is sufficient, accuracy is, however, required during surgery in which spot-checking can be used to determine whether tissue can remain viable or needs to be removed.

Pulse oximeters and tissue oximeters are two types of oximeters that operate on different principles. A pulse oximeter requires a pulse in order to function. A pulse oximeter typically measures the absorbance of light due to pulsing arterial blood. In contrast, a tissue oximeter does not require a pulse in order to function, and can be used to make tissue oxygen saturation measurements of a tissue flap that has been disconnected from a blood supply.

Human tissue, as an example, includes a variety of light-absorbing molecules. Such chromophores include oxygenated and deoxygenated hemoglobins, melanin, water, lipid, and cytochrome. Oxygenated and deoxygenated hemoglobins are the most dominant chromophores in tissue for much of the visible and near-infrared spectral range. Light absorption differs significantly for oxygenated and deoxygenated hemoglobins at certain wavelengths of light. Tissue oximeters can measure oxygen levels in human tissue by exploiting these light-absorption differences.

Despite the success of existing oximeters, there is a continuing desire to improve oximeters by, for example, by providing oximeters that have source-to-detector distances that are selectable for analyzing specific tissue depths, that emit wavelengths of light (visible light, IR, or both) that can be user selected for probing different tissue depth, or both. Therefore, there is a need for an improved tissue oximetry devices and methods of making measurements using these devices.

BRIEF SUMMARY OF THE INVENTION

An oximeter probe having source-to-detector distances that are user selectable is provided for analyzing specific tissue depths of tissue, that emits wavelengths of light (visible light, IR, or both) that can be user selected for probing different tissue depth, or both. The oximeter probe has self-contained optics (sources and detectors), computer processing, a display, and a power-supply (battery) for self-contained use.

The selectable tissue depth analysis allows a user to make oximetry measurements of specific tissue depths that can be varied while using the oximeter. For example, the oximeter can be set to make oximeter measurements on a tissue flap that is being used to reconstruct tissue, such as breast tissue, and can be used to make oximeter measurements of the tissue below the tissue flap that that the flap is being attached to. Thereby, a user can determine whether the tissue flap is healthy and can be used for reconstruction, and whether the tissue to which the tissue flap is being connected is suitably healthy so that the tissue flap can survive reattachment to the patient.

In an implementation, a method includes: providing a handheld oximeter housing; providing a processor housed in the handheld oximeter housing; providing a memory, housed in the handheld oximeter housing, connected to the processor; providing a display, accessible from an exterior of the handheld oximeter housing, connected to the processor; and providing a battery, housed in the handheld oximeter housing.

The method further includes: allowing for the battery to supply power to the processor, the memory, and the display; providing a first probe tip including a first source structure and a first number of detector structures having a first arrangement; coupling the first probe tip to the handheld oximeter housing; providing a second probe tip including a second source structure and a second number of detector structures having a second arrangement, where the first and second arrangements are different arrangements; and replacing the first probe tip with the second probe tip via coupling the second probe tip to the handheld oximeter housing such that the first arrangement is changed to the second arrangement.

In an implementation, a method includes: using an oximeter to determine an oxygen saturation of a tissue to be measured, where the oximeter includes a processor, memory, display, power source, and probe tip including a first source structure and a number of detector structures, the processor is connected to the memory and display, and the power source is connected to the processor, memory, and display; emitting first light by the first source structure into the tissue to be measured and detecting a reflection of the first light from the tissue by the detector structures that are closer to the source structure than a threshold distance;

fitting first detector responses, generated by the detector structures that are closer to the source structure than the threshold distance based on the detected first light, to a number of simulated reflectance curves stored in the memory; and determining first measurement information for first tissue of the tissue to be measured based on one or more best fitting ones of the simulated reflectance curve to the first detector responses.

The method further includes: emitting second light by the first source structure into the tissue and detecting a reflection of the second light from the tissue by the detector structures that are farther from the source structure than a threshold distance; fitting second detector responses, that are generated by the detector structures that are farther from the source structure than the threshold distance based on the detected second light, to the number of simulated reflectance curves stored in the memory; determining second measurement information based on one or more best fitting ones of the simulated reflectance curve to the second detector responses; and determining second measurement information for second tissue of the tissue to be measured based on the second light detected by the detector structures that are farther from the source structure than the threshold distance.

The method further includes: based on the first measurement information, calculating and displaying on the display a first oxygen saturation measurement for a first tissue region below a surface of the tissue at a first depth; based on the second measurement information, calculating and displaying on the display a second oxygen saturation measurement for a second tissue region below the surface of the tissue at a second depth; and based on the first measurement information and the second measurement information, calculating and displaying on the display a third oxygen saturation measurement for a third tissue region below the surface of the tissue at a combination of the first and second depths, where the first tissue is a first depth below the surface of the tissue to be measured, the second tissue is a second depth below the surface of the tissue to be measured, and the first depth is less than the second depth.

In an implementation, a method includes: providing an oximeter to determine an oxygen saturation of a tissue to be measured, where the oximeter includes a processor, memory, display, power source, and probe tip including a first source structure and a number of detector structures, the processor is coupled to the memory and display, and the power source is coupled to the processor, memory, and display; and before using the oximeter to make a determination of oxygen saturation, inserting and enclosing the oximeter into a probe cover, where the probe includes a first portion of the probe cover, where the first portion includes a first open end and a first closed end, opposite to the first open end, and the first closed end includes a display viewer panel, and a second portion of the probe cover, where the second portion includes a second open end and a second closed end, opposite to the second open end, the second closed end includes an optical sensor panel, and coupling of the first open end to the second open end forms a sealed probe cover enclosure for the oximeter device.

The method further includes: while the oximeter is enclosed in the probe cover, emitting first light by the first source structure into the tissue to be measured and detecting a reflection of the first light from the tissue by the detector structures that are closer to the source structure than a threshold distance; fitting first detector responses, generated by the detector structures that are closer to the source structure than the threshold distance based on the detected first light, to a number of simulated reflectance curves stored in the memory; and determining first measurement information for first tissue of the tissue to be measured based on one or more best fitting ones of the simulated reflectance curve to the first detector responses.

The method further includes: while the oximeter is enclosed in the probe cover, emitting second light by the first source structure into the tissue and detecting a reflection of the second light from the tissue by the detector structures that are farther from the source structure than a threshold distance; fitting second detector responses, that are generated by the detector structures that are farther from the source structure than the threshold distance based on the detected second light, to the number of simulated reflectance curves stored in the memory; and determining second measurement information based on one or more best fitting ones of the simulated reflectance curve to the second detector responses.

The method further includes: determining second measurement information for second tissue of the tissue to be measured based on the second light detected by the detector structures that are farther from the source structure than the threshold distance; based on the first measurement information, calculating and displaying on the display a first oxygen saturation measurement for a first tissue region below a surface of the tissue at a first depth; based on the second measurement information, calculating and displaying on the display a second oxygen saturation measurement for a second tissue region below the surface of the tissue at a second depth; and based on the first measurement information and the second measurement information, calculating and displaying on the display a third oxygen saturation measurement for a third tissue region below the surface of the tissue at a combination of the first and second depths, where the first tissue is a first depth below the surface of the tissue to be measured, the second tissue is a second depth below the surface of the tissue to be measured, and the first depth is less than the second depth.

Other objects, features, and advantages of the present invention will become apparent upon consideration of the following detailed description and the accompanying drawings, in which like reference designations represent like features throughout the figures.

DETAILED DESCRIPTION OF THE INVENTION

The present invention generally relates to a wireless, handheld oximeter probe for measuring tissue oxygen. The oximeter probe has a source and a number of detectors that can be variously accessed for measuring tissue oxygen saturation from different tissue depths of tissue.

Figure 1A:
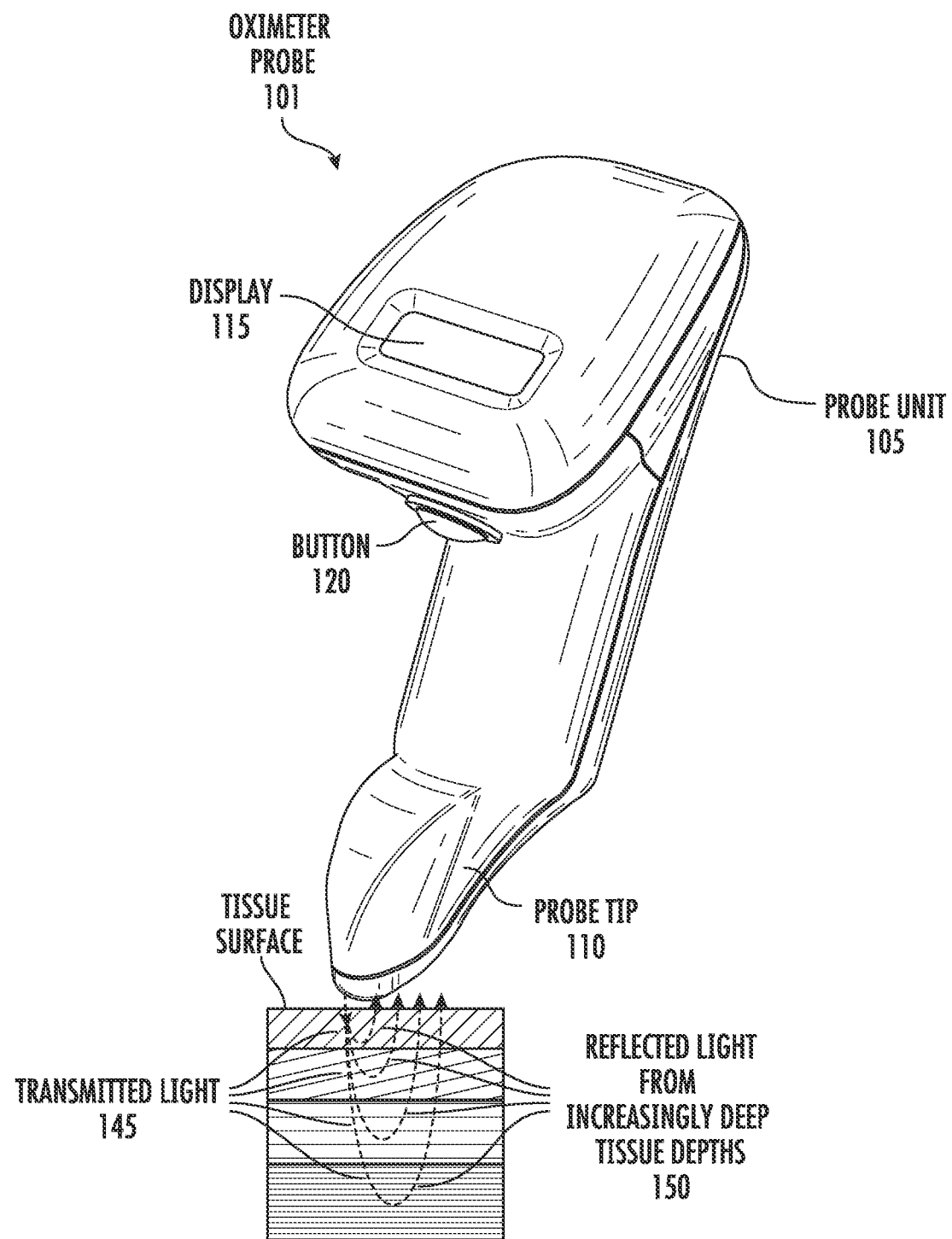
FIG. 1A shows an oximeter probe and emitted radiation and detected radiation for probing a number of tissue depths.

FIG. 1A shows a handheld oximeter probe 101. This oximeter probe is used to make tissue oxygen saturation measurements of target tissue. In an implementation, the oximeter probe is a tissue oximeter, but in other implementation, the oximeter probe can be a pulse oximeter. Oximeter probe 101 has two portions, a probe unit 105 and probe tip 110.

The handheld oximeter probe can be used in a variety of environments, such as surgical, sterile environment for spot measurements, doctors offices, at sporting events (e.g., personal and professional sports uses), homes, retirement communities, hospice care, first responders (e.g., paramedics, emergency medical technicians, ambulance care, and fire fighters), pre-operative care, post-operative care, pediatric care, geriatric care, medical rehabilitation centers, veterinary uses, and other users. The use environments can also range from sterile, to generally sanitary and cleanly environments (e.g., non-sterile recovery rooms in a hospital, doctors offices, and other medical offices, home use, and other environments), and to environments that are typically not sanitary, such as mud, dirt, sand, and dusty environments, snow (e.g., ski areas, ski patrol, and mountain climbing), rain, ice, and near bodies of water (e.g., at swimming pools, beaches, and boats).

The oximeter probe has a display 115 (e.g., an LCD display) and a button 120. When the button is depressed, light is emitted at the probe tip into a target tissue to be measured, and reflected light from the target tissue is received at probe tip. The transmitted and received light are processed by the oximeter probe to determine a tissue oxygen saturation of the tissue. From the received light, the probe determines a measured tissue oxygen saturation for the tissue. An indicator (e.g., a numerical value) for the measured tissue oxygen saturation is displayed on the display.

The oximeter probe is shaped ergonomically to comfortably fit in a user's hand. During use, the probe is held in a user's hand between a user's thumb and fingers. The display faces toward the user's eyes when a face (not shown) of the probe tip is directed away from the user and faces toward the target tissue to be measured.

In an implementation, light 145 is transmitted from a source in the probe tip into the target tissue, and light 150 is reflected back to the probe tip where the light is detected by one or more detectors. The detectors are located at increasing distances from the source. Light detected by the detectors is reflected back from depths within the tissue that increase with the increasing distances of the detectors from the source.

The probe unit can collect measurement information for the reflected light from one of the detectors or a combination of detectors for determining the tissue oxygen saturation at different tissue depths.

Figure 1B:
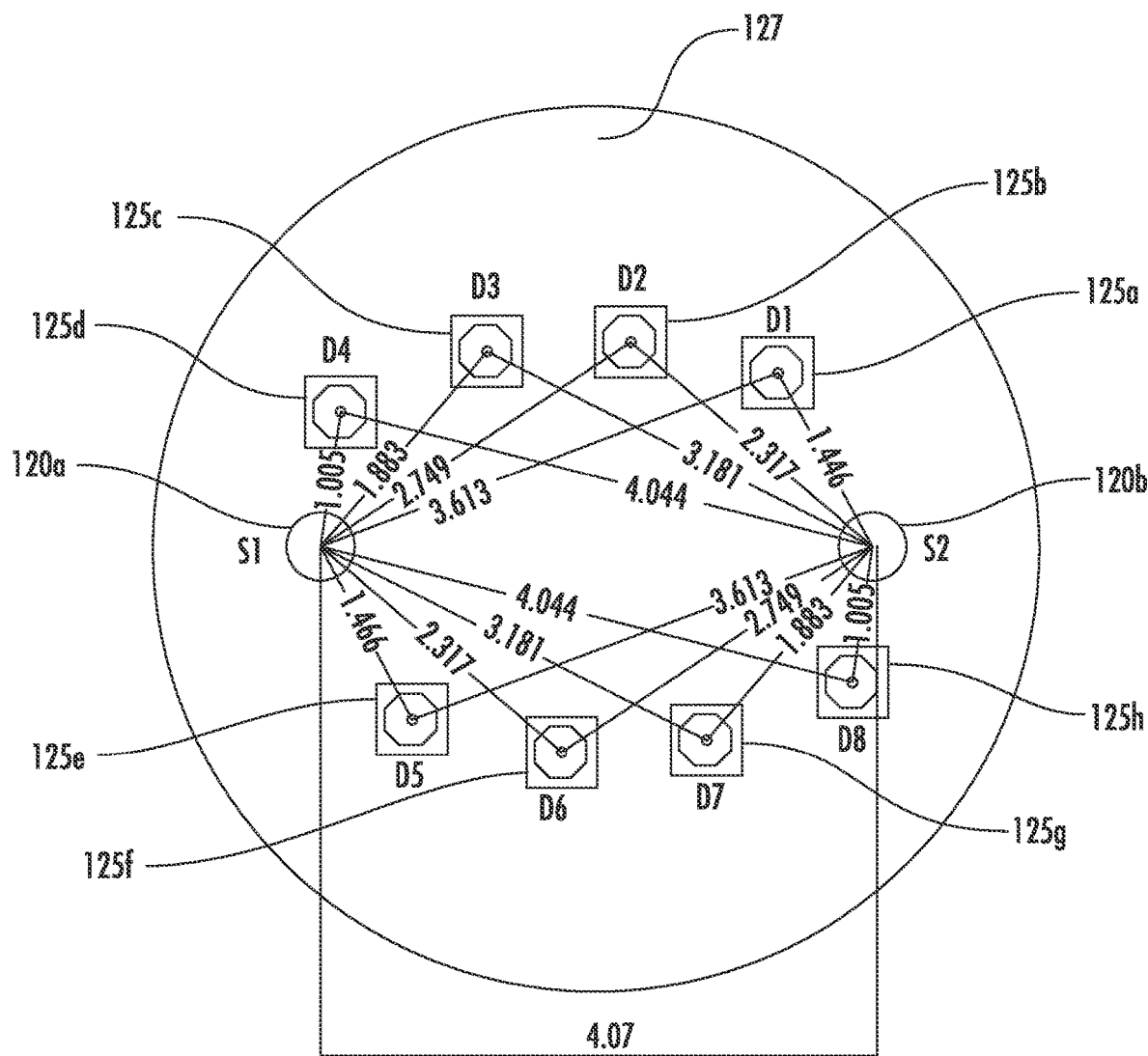
FIG. 1B shows an end view of the probe tip in an implementation.

FIG. 1B shows an end view of probe tip 110 in an implementation. Probe tip 110 is configured to contact tissue (e.g., a patient's skin) for which a tissue oximetry measurement is to be made. Probe tip 110 includes first and second source structures 120a and 120b (generally source structures 120) and includes first, second, third, fourth, fifth, sixth, seventh, and eighth detector structures 125a-125h (generally detector structures 125). In alternative implementations, the oximeter probe includes more or fewer source structures, includes more or fewer detector structures, or both.

Each source structure 120 is adapted to emit light (such as infrared light) and includes one or more light sources, such as four light sources that generate the emitted light. Each light source can emit one or more wavelengths of light. Each light source can include a light emitting diode (LED), a laser diode, an organic light emitting diode (OLED), a quantum dot LED (QMLED), or other types of light sources.

Each source structure can include one or more optical fibers that optically link the light sources to a face 127 of the probe tip. In an implementation, each source structure includes four LEDs and includes a single optical fiber that optically couples the four LEDs to the face of the probe tip. In alternative implementations, each source structure includes more than one optical fiber (e.g., four optical fibers) that optically couples the LEDs to the face of the probe tip.

Each detector structure includes one or more detectors. In an implementation, each detector structure includes a single detector adapted to detect light emitted from the source structures and reflected from tissue. The detectors can be photodetectors, photoresistors, or other types of detectors. The detector structures are positioned with respect to the source structures such that two or more (e.g., eight) unique source-to-detector distances are created.

In an implementation, the shortest source-to-detector distances are approximately equal. For example, the shortest source-to-detector distances are approximately equal between source structure 120a and detector structure 125d (S1-D4) and between source structure 120b and detector structure 125a (S2-D8) are approximately equal. The next longer source-to-detector distances (e.g., longer than each of S1-D4 and S2-D8) between source structure 120a and detector structure 125e (S1-D5) and between source structure 120b and detector structure 125a (S2-D1) are approximately equal. The next longer source-to-detector distances (e.g., longer than each of S1-D5 and S2-D1) between source structure 120a and detector structure 125c (S1-D3) and between source structure 120b and detector structure 125g (S2-D7) are approximately equal. The next longer source-to-detector distances (e.g., longer than each of S1-D3 and S2-D7) between source structure 120a and detector structure 125f (S1-D6) and between source structure 120b and detector structure 125b (S2-D2) are approximately equal. The next longer source-to-detector distances (e.g., longer than each of S1-D6 and S2-D2) between source structure 120a and detector structure 125c (S1-D2) and between source structure 120b and detector structure 125f (S2-D6) are approximately equal. The next longer source-to-detector distances (e.g., longer than each of S1-D2 and S2-D6) between source structure 120a and detector structure 125g (S1-D7) and between source structure 120b and detector structure 125c (S2-D3) are approximately equal. The next longer source-to-detector distances (e.g., longer than each of S1-D7 and S2-D3) between source structure 120a and detector structure 125a (S1-D1) and between source structure 120b and detector structure 125e (S2-D5) are approximately equal. The next longer source-to-detector distances (e.g., longest source-to-detector distance, longer than each of S1-D1 and S2-D5) between source structure 120a and detector structure 125h (S1-D8) and between source structure 120b and detector structure 125d (S2-D4) are approximately equal. In other implementations, the source-to-detector distance can all be unique or have fewer then eight distances that are approximately equal.

Table 1 below shows the eight unique source-to-detector distances according to an implementation. The increase between nearest source-to-detector distances is approximately 0.4 millimeters.

TABLE 1

| Source-to-Detector Pairs | Source-to-Detector Distances Millimeters |
|---|---|
| (S1-D4) | 1.005 |
| (S2-D8) | 1.005 |
| (S1-D5) | 1.446 |
| (S2-D1) | 1.446 |
| (S1-D3) | 1.883 |
| (S2-D7) | 1.883 |
| (S1-D6) | 2.317 |
| (S2-D2) | 2.317 |
| (S1-S2) | 2.749 |
| (S1-S2) | 2.749 |
| (S1-D7) | 3.181 |
| (S2-D3) | 3.181 |
| (S1-D1) | 3.613 |
| (S2-D5) | 3.613 |
| (S1-D8) | 4.004 |
| (S2-D4) | 4.004 |

In an implementation, detector structures 125a and 125e are symmetrically positioned about a point that is on a straight line connecting sources 120a and 120b. Detector structures 125b and 125f are symmetrically positioned about the point. Detector structures 125c and 125g are symmetrically positioned about the point. Detector structures 125d and 125h are symmetrically positioned about the point. The point can be centered between source structures 120a and 120b on the connecting line.

A plot of source-to-detector distance verses reflectance detected by detector structures 125 can provide a reflectance curve where the data points are well spaced along the x-axis. These spacings of the distances between source structures 120a and 120b, and detector structures 125 reduces data redundancy and can lead to the generation of relatively accurate reflectance curves.

In an implementation, the source structures and detector structures can be arranged at various positions on the probe surface to give the distances desired (such as indicated above). For example, the two sources form a line, and there will be equal number of detectors above and below this line. And the position of a detector (above the line) will have point symmetry with another detector (below the line) about a selected point on the line of the two sources. As an example, the selected point may be the middle between the two sources, but not necessarily. In other implements, the positioning can be arranged based on a shape, such as a circle, an ellipse, an ovoid, randomly, triangular, rectangular, square, or other shape.

The following patent applications describe various oximeter devices and oximetry operation, and discussion in the following applications can be combined with aspects of the invention described in this application, in any combination. The following patent application are incorporated by reference along with all references cited in these application Ser. No. 14/944,139, filed Nov. 17, 2015, Ser. No. 13/887,130 filed May 3, 2013, Ser. No. 15/163,565, filed May 24, 2016, Ser. No. 13/887,220, filed May 3, 2013, Ser. No. 15/214,355, filed Jul. 19, 2016, Ser. No. 13/887,213, filed May 3, 2013, Ser. No. 14/977,578, filed Dec. 21, 2015, Ser. No. 13/887,178, filed Jun. 7, 2013, Ser. No. 15/220,354, filed Jul. 26, 2016, Ser. No. 13/965,156, filed Aug. 12, 2013, Ser. No. 15/359,570, filed Nov. 22, 2016, Ser. No. 13/887,152, filed May 3, 2013, Ser. No. 29/561,749, filed Apr. 16, 2016, 61/642,389, 61/642,393, 61/642,395, 61/642,399 filed May 3, 2012, and 61/682,146, filed Aug. 10, 2012.

Figure 1C:
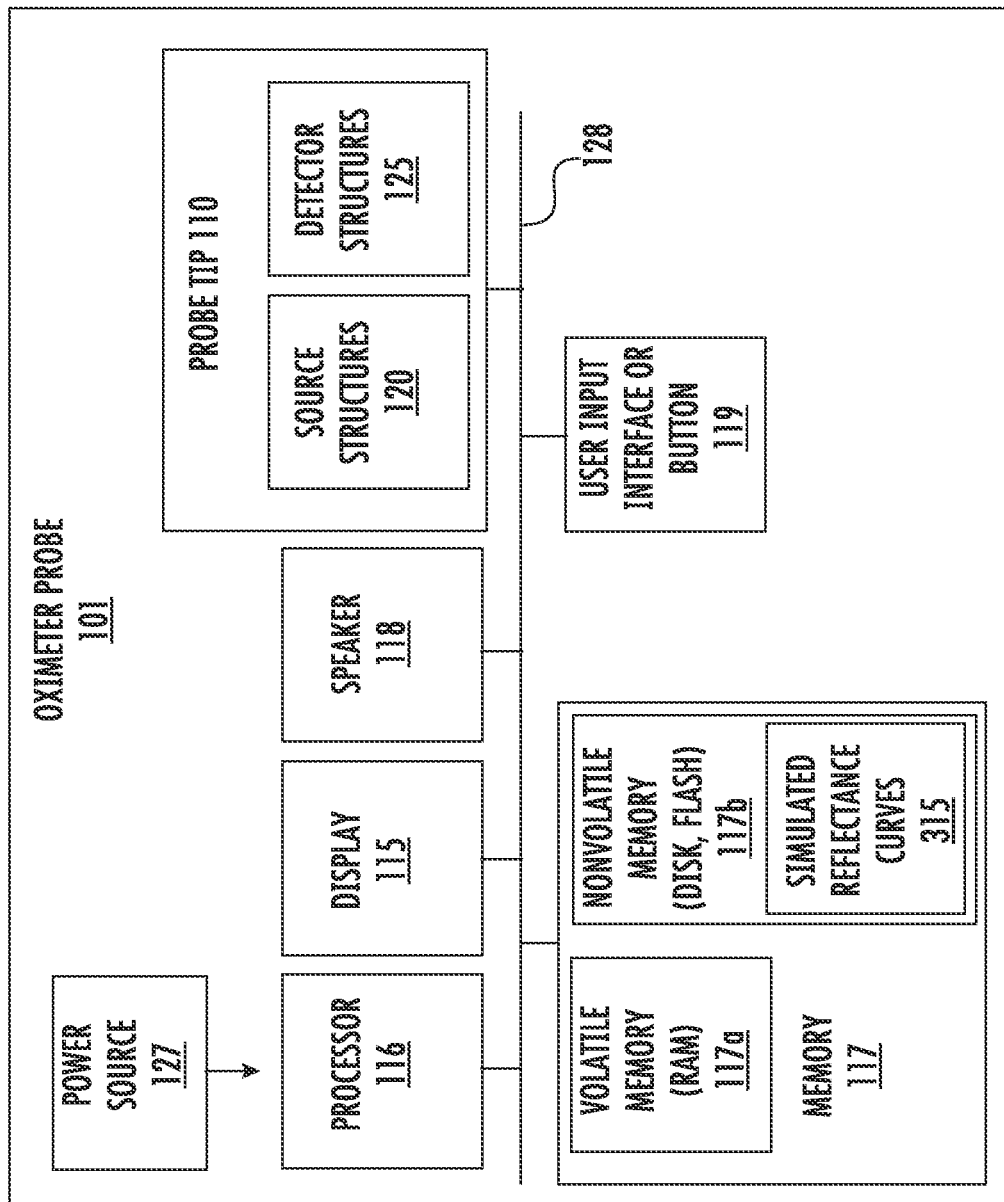
FIG. 1C shows a block diagram of oximeter probe 101 in an implementation.

FIG. 1C shows a block diagram of oximeter probe 101 in an implementation. Oximeter probe 101 includes display 115, a processor 116, a memory 117, a speaker 118, one or more user-selection devices 119 (e.g., one or more buttons, switches, touch input device associated with display 115), a set of source structures 120, a set of detector structures 125, and a power source (e.g., a battery) 127. The foregoing listed components may be linked together via a bus 128, which may be the system bus architecture of oximeter probe 101. Although this figure shows one bus that connects to each component, the busing is illustrative of any interconnection scheme serving to link these components or other components included in oximeter probe 101. For example, speaker 118 could be connected to a subsystem through a port or have an internal direct connection to processor 116. Further, the components described are housed in a mobile housing (see FIG. 1) of oximeter probe 101 in an implementation.

Processor 116 may include a microprocessor, a microcontroller, a multi-core processor, or other processor type. Memory 117 may include a variety of memories, such as a volatile memory 117a (e.g., a RAM), a nonvolatile memory 117b (e.g., a disk or FLASH). Different implementations of oximeter probe 101 may include any number of the listed components, in any combination or configuration, and may also include other components not shown.

Power source 127 can be a battery, such as a disposable battery. Disposable batteries are discarded after their stored charge is expended. Some disposable battery chemistry technologies include alkaline, zinc carbon, or silver oxide. The battery has sufficient stored charged to allow use of the handheld device for several hours.

In other implementations, the battery is rechargeable where the battery can be recharged multiple times after the stored charge is expended. Some rechargeable battery chemistry technologies include nickel cadmium (NiCd), nickel metal hydride (NiMH), lithium ion (Li-ion), and zinc air. The battery can be recharged, for example, via an AC adapter with cord that connects to the handheld unit. The circuitry in the handheld unit can include a recharger circuit (not shown). Batteries with rechargeable battery chemistry may be sometimes used as disposable batteries, where the batteries are not recharged but disposed of after use.

Figure 2:
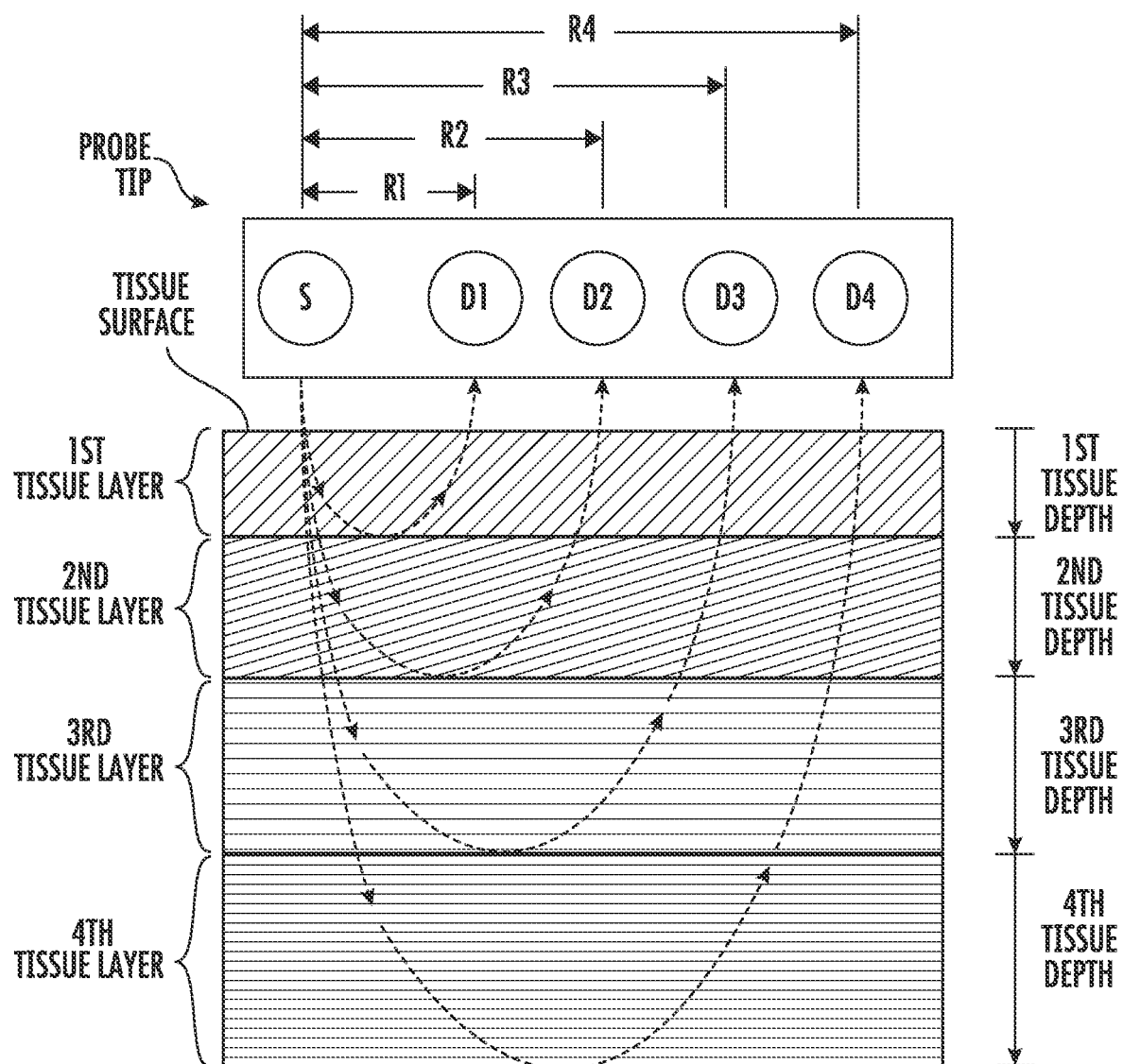
FIG. 2 shows a diagram of different tissue depths that can analyzed by the oximeter probe.

FIG. 2 shows a diagram of a probe tip that include one source S and four of detectors D1, D2, D3, and D4 in an implementation. The detectors are located at increasing fixed distances (R1<R2<R3<R4) from the source. Detector D1, located at R1, is closest to the source and detects light that reflects within a first tissue layer that extends from the tissue surface to a first tissue depth. Detector D2, located at R2, detects light that reflects within a second tissue layer that extends from the first tissue depth to a second tissue depth. The second tissue depth is deeper from the tissue surface than the first tissue depth. Detector D3, located at R3, detects light that reflects within a third tissue layer that extends from the second tissue depth to a third tissue depth. The third tissue depth is deeper from the tissue surface than the second tissue depth. Detector D4, located at R4, detects light that reflects within a fourth tissue layer that extends from the third tissue depth to a fourth tissue depth where the fourth tissue depth is deeper from the tissue surface than the third tissue depth. The oximeter probe uses the measurement information collected from one or more of these detectors to determine tissue oxygen saturation for one or more of the tissue depths.

While FIG. 2 shows that the probe tip includes a single detector for each tissue layer, the probe tip can include a number of detectors for each tissue layer, such as 2 detectors, 3 detectors, 4 detectors, 5 detectors, 6 detectors, 7 detectors, 8 detectors, 9 detectors, 10 detectors, or more detectors for each tissue layer. The probe tip can also include more than one source, such as 2 sources, 3 sources, 4 sources, 5 sources, 6 sources, 7 sources, 8 sources, 9 sources, 10 sources, or more sources. The arrangement of sources and detectors can be the arrangement of FIG. 1B where there are eight unique source to detector distances and each source to detector distance is duplicated at least once.

Figure 3:
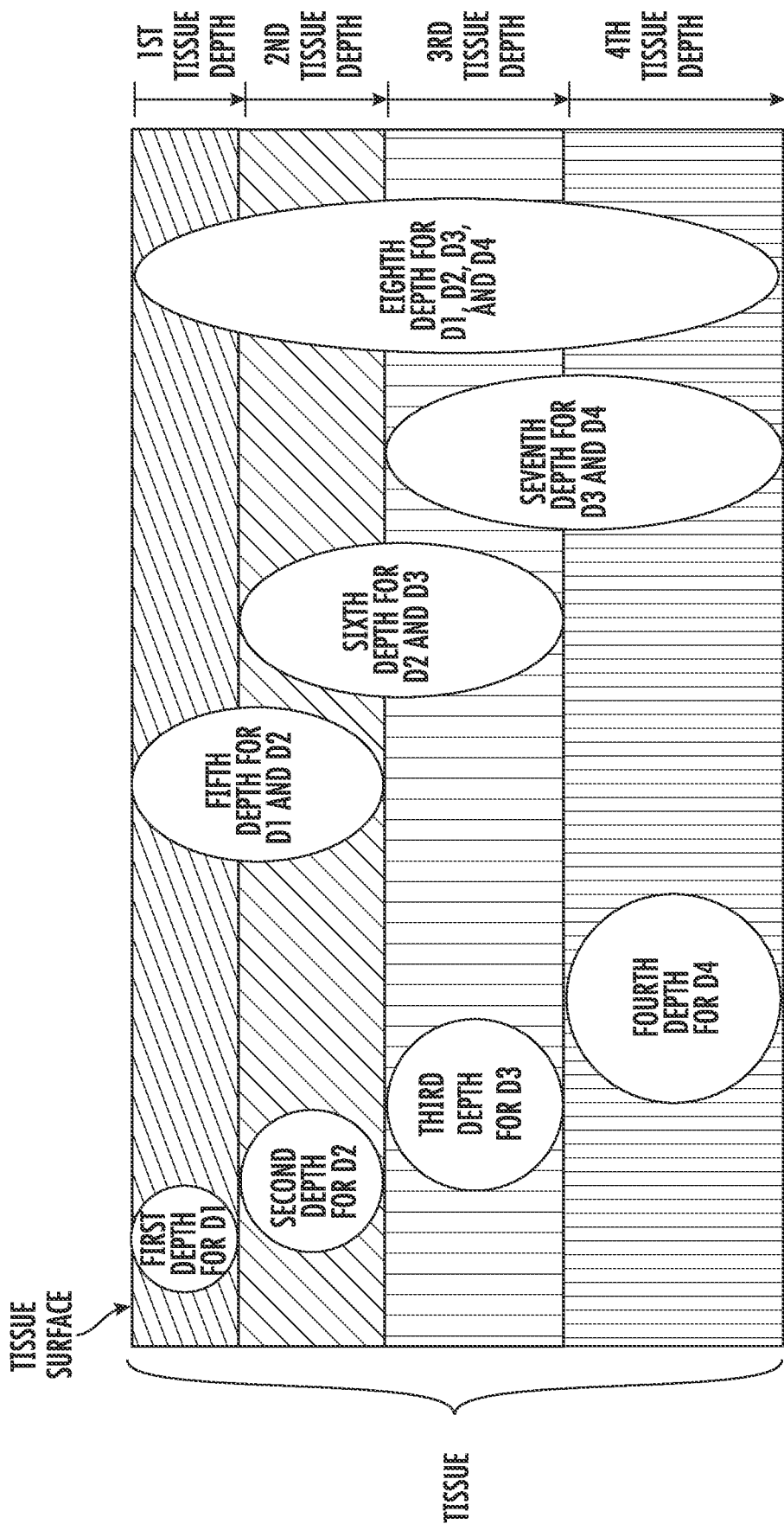
FIG. 3 shows another diagram of different tissue depths of tissue probed by the oximeter probe using single detectors and combinations of detectors.

FIG. 3 shows a number of different tissue depths than can be analyzed by the oximeter probe for measurement information collected from a single detector or combinations of detectors. For example, tissue oxygen saturation can be determined for the first, second, third, and fourth tissue layers by collecting measurement information respectively from detectors D1, D2, D3, and D4. Tissue oxygen saturation can also be determined for the fifth, sixth, seventh, and eighth tissue layers by collecting measurements respectively from combinations of detectors: D1-D2; D2-D3; D3-D4; and D1-D4.

It can be appreciated that probe tips can include more than one source and greater or less then four detectors for determining tissue oxygen saturation for various tissue depths. It can also be appreciated that two more of the source-to-distance can be the same. For example, redundant source-to-detector distances can be used for calibration purposes or for self-checks of collected data.

In an implementation, the oximeter probe uses spatially resolved spectroscopy to determine tissue oxygen saturation information for the different tissue depths. Specifically, the oximeter probe uses: stored source-to-detector distances for the sources and detectors, measurement information collected from one or more of the detectors for reflected light, and a spatially resolved spectroscopy method for calculating the tissue oxygen saturation information.

Figure 4:
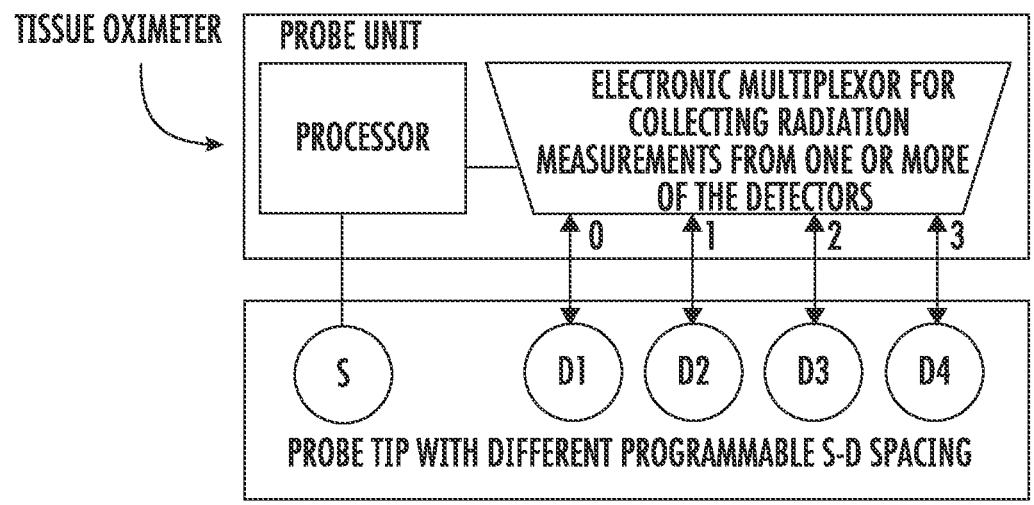
FIG. 4 is a block diagram of an oximeter probe in an implementation.

FIG. 4 is a block diagram of an oximeter probe in an implementation. The probe unit of the oximeter probe includes a processor and a multiplexer that is electronically coupled to the processor. The probe tip includes the source S and the detectors D1-D4. The probe unit also includes an analog-to-digital converter (not shown) in the electronic path between the detectors and the processor. The probe tip can include more sources and more or fewer detectors, such as the configuration of two sources and eight detectors shown in FIG. 1B and described above.

The processor controls the multiplexer to selectively collect measurement information for the reflected light that is detected by one or more of the detectors. The processor uses the measurement information to determine tissue oxygen saturation for one or more of the tissue depths of the tissue.

In an implementation that includes more than one source, the sources can be controlled by the processor such that one source is activated to emit light, two sources are activated to emit light, three sources are activated to emit light, or a greater number of sources are activated to emit light. The processor can allow data collection from one or more of the detectors for one or more of the sources that emit light such that the tissue can be probed at different depths to thereby determine oxygen saturation at the different tissue depths, such as described above with respect to FIGS. 2-3.

Figure 5:
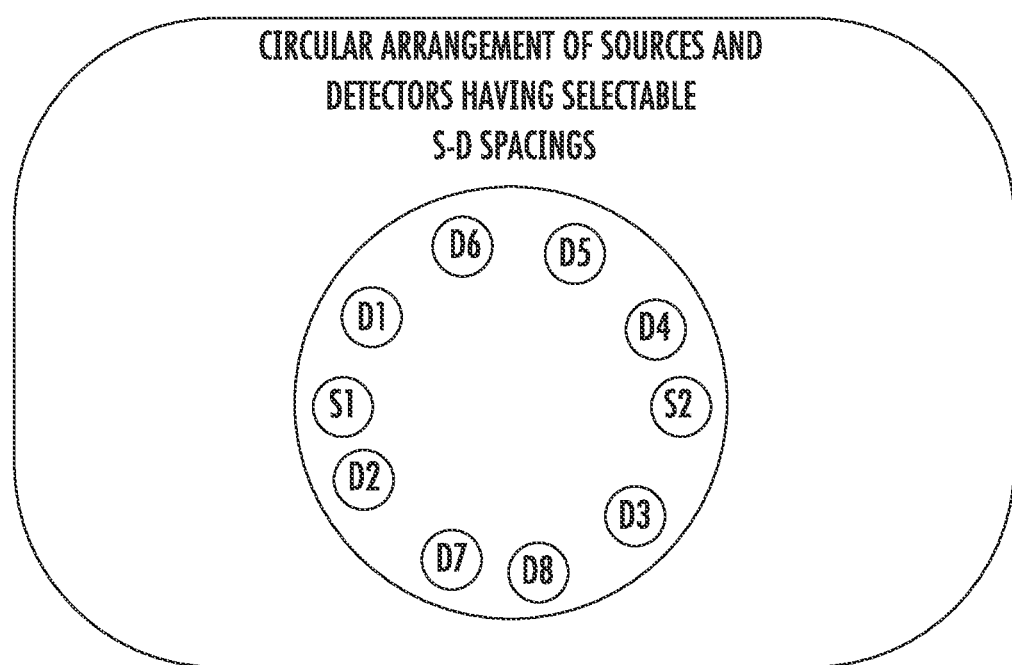
FIG. 5 shows the probe face of a probe tip that includes two sources S1 and S2 and eight detectors D1-D8 in a circular configuration.

FIG. 5 shows the probe face of a probe tip that includes two sources S1 and S2 and eight detectors D1-D8 in an implementation. The sources and detectors are arranged in a circular configuration. The probe face can include more or fewer sources and more or fewer detectors. The processor controls the multiplexer to transmit measurement information to the processor from one or more of the detectors for light emitted from one or both of the sources. In alternative implementations, the sources and detectors are arranged in other configurations, such as trapezoid, rectangle, square, triangular, linear, arbitrary, oval, elliptical, one or more combinations of these shapes, or other shapes. The sources and detectors can also be arranged in a nonplanar configurations, such as on a curved surface, where a curve of the curve surface can complement that shape of a body part, such as the curve of a neck, head, knee, elbow, foot, or other body part to conform the sources and detectors to the curved shapes.

Figure 6:
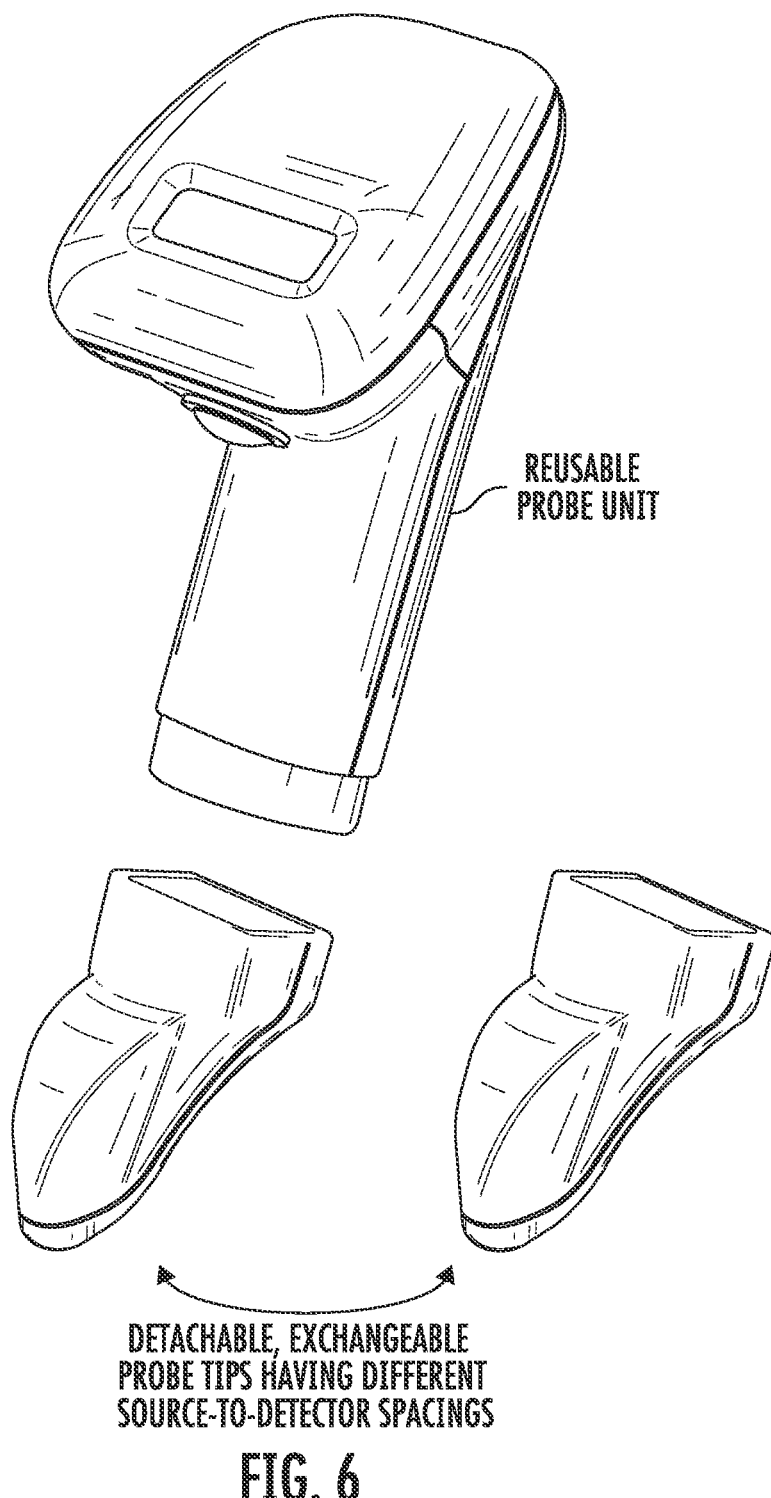
FIG. 6 shows an oximeter probe where the probe tip is detachable from the probe unit and where the probe unit can be replaced with a different probe tip.

FIG. 6 shows an oximeter probe 601 where the probe tip 605 is detachable from the probe unit 610. Probe tip 605 can be detached and replaced with a different probe tip 615 where the two probe tips have different source-to-detector spacings. For example, a first probe tip can have the configuration of sources and detectors of the probe tip shown in FIG. 1B and a second probe tip can have the configuration of sources and detector of the probe tip shown in FIG. 5. The two different probe tips can be used with the probe unit as a formed oximeter probe to determine tissue oxygen saturation for different tissue depths. In an implementation, the different probe tips have a different number of sources, a different number of detectors, or both a different number of sources and a different number of detectors.

Figure 7:
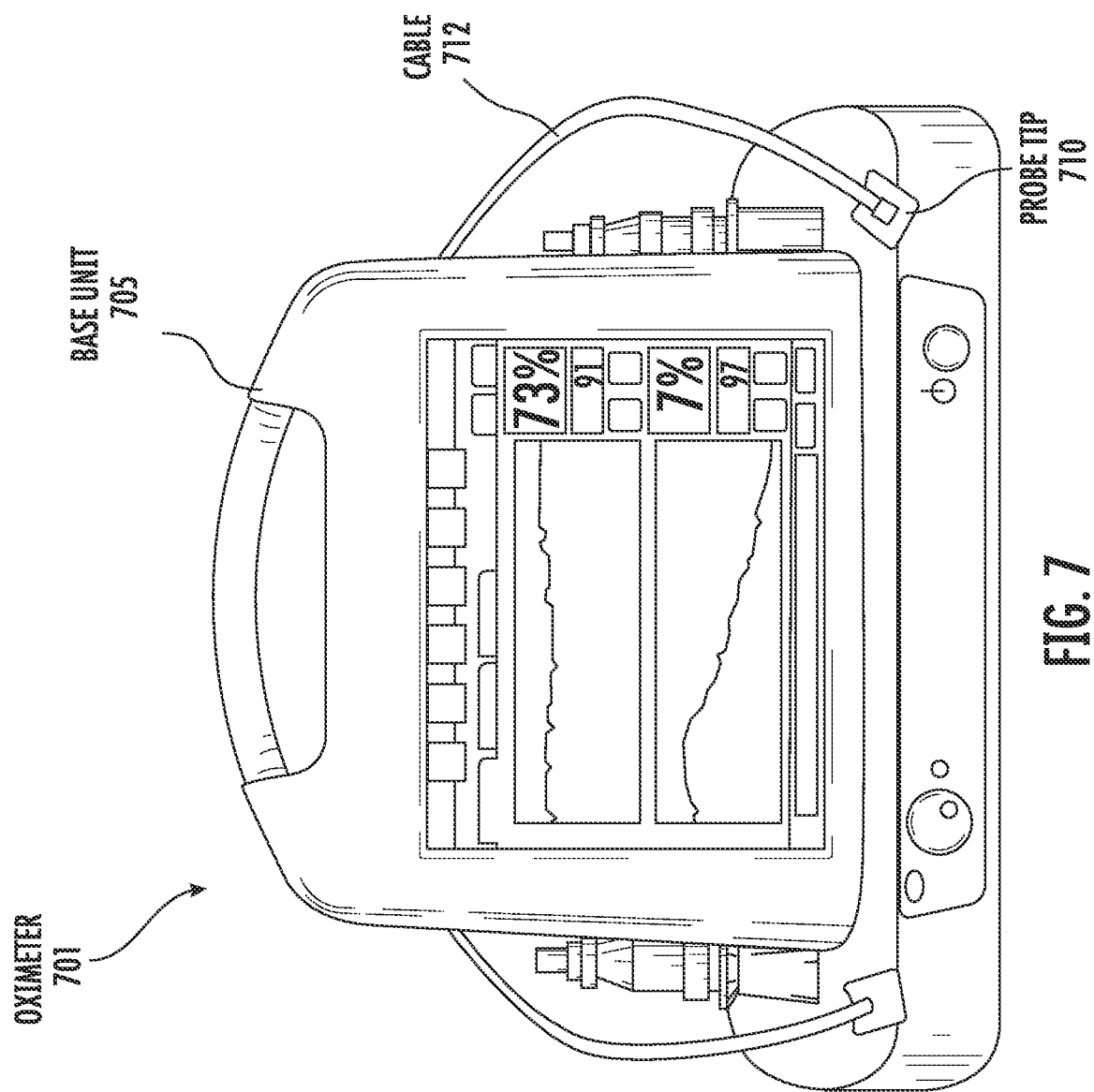
FIG. 7 shows a tissue oximeter that includes a base unit and a detachable cable that includes a probe tip.

FIG. 7 shows a tissue oximeter 701 that includes a base unit 705 and a detachable cable 712 that includes a probe tip 710 attached to an end of the cable. The probe tip includes one or more sources and one or more detectors. The one or more sources and one or more detectors are separated by a number of different source-to-detector distances. The source-to-detectors distances between sources emitting light and detectors detecting light can be variously set for probing tissue at different tissue depths below the surface of the tissue. The base unit can be configured, for example by a user, such that one or more of the sources is configured to transmit light and one or more of the detectors is configured to detect the light subsequent to reflection.

The base unit includes one or more user interfaces for receiving user input for selecting one or more sources for emitting light and for receiving user input for selecting one or more of detector for detecting light. The one or more user interfaces of the base unit adapted to receive user input can include buttons, a touch interface display, dials, switches, or other interfaces. The base unit can include one or more communication ports adapted to receive information from a connected computing device for selecting one or more sources for emitting light and one or more detectors for detecting the light.

In an implementation, the cable and probe tip are detachable from the base unit and can be replaced with a different cable and probe tip. The two different probe tips of the two different cables have one or more different source-to-detector distances between one or more sources and one or more detectors for probing different tissue depths.

Figure 8:
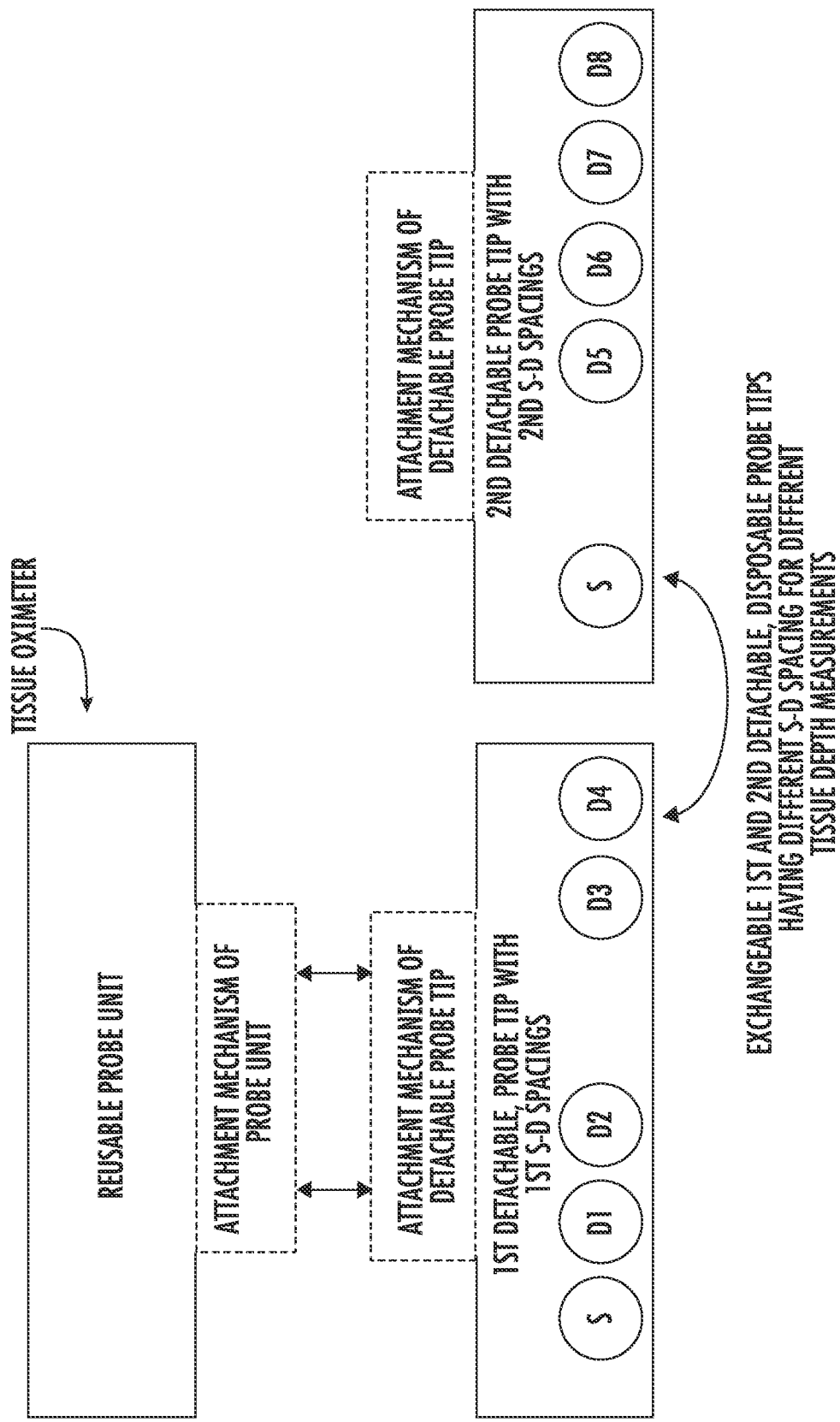
FIG. 8 shows a block diagram of two different probe tips having two different source-to-detector spacings.

FIG. 8 shows a block diagram of two different probe tips having two different source-to-detector spacings. The probe tips include one source and four detectors. The probe tips can be switched so that different tissue depths of tissue can be probed by the tissue oximeter. For example, the oximeter probe with the first probe tip can probe relatively shallow and deep tissue depths, whereas the oximeter probe with the second probe tip can probe relatively deep and intermediate tissue depths. It will be appreciated that the probe tips can include more than one source and fewer or more detectors. In an implementation, each probe tip has an arrangement of one more sources and one or more detectors in a circular arrangement.

In an implementation, a distance between at least one of the sources and at least one of the detectors is approximately 200 micrometers or less, such as 150 micrometers or less, 100 micrometers or less, 75 micrometers or less, or other distances. At least one of the sources that is positioned 200 micrometers or less from one of the detectors emits visible light, infrared light, or both. Light emitted in the visible spectrum can include wavelengths between blue light and red or light having wavelengths of less than 580 nanometers, or both, such as green light, orange light, yellow light, or other colors of light having wavelengths between the wavelengths of blue light and red light.

Light of relatively shorter wavelengths (e.g., wavelengths between blue light and red light) may be transmitted from the probe tip for probing the thin, top layers of tissue (e.g., 20 micrometers to about 150 micrometers, or less), such as the epidermis. These relatively shorter wavelengths of light tend to penetrate less deeply into the dermis or not penetrate the dermis so that measurement information from the dermis from these shorter wavelengths of light does not significantly contribute to the measurement information from the epidermis. Therefore, chromophores in the epidermis, such as melanin, can be probed by the oximeter probe, and chromophores in the dermis may not contribute to measurements for melanin in the epidermis.

Light having relatively longer wavelengths can be selected for probing relatively deeper into the tissue, such as deeper than about 20 micrometers, deeper than about 50 micrometers, deeper than about 75 micrometers, deeper than about 100 micrometers, deeper than about 125 micrometers, or deeper than about 150 micrometers (e.g., deeper than the tissue depth of the epidermis, such as into the dermis, subcutaneous fat, or both).

In an implementation, measurement information for substantially all of the wavelengths of light (e.g., visible light, IR, or both) is transmitted from the sources into tissue and detected by the detectors. Reflectance data generated by the detectors for each of the wavelengths can be analyzed, such as by fitting the reflectance data to simulated reflectance curves to determine measurement values (e.g., absorption coefficients, reduced scattering coefficients, melanin concentration, oxygen saturation, blood volume, any combination of these measurements, or other measurements). Thereafter, the processor can use the measured values, the reflectance data, or other information to determine measured values for the various tissue layers at various tissue depths. For example, the processor can then determine one or more measurement values (e.g., absorption coefficients, reduced scattering coefficients, melanin concentration, oxygen saturation, blood volume, any combination of these measurements, or other measurements) for the epidermis that are substantially independent of measurement values for chromophores in the dermis. Fitting the reflectance data to the simulated reflectance curves is describe further below.

The processor can also determine one or more measurement values (e.g., oxygen saturation value) for the dermis that are substantially independent of measurement values for chromophores in the epidermis.

In an implementations, select wavelengths (e.g., relatively short wavelengths, such as between blue and red, or relatively long wavelengths, such as red, IR, or both) can be transmitted from the sources and detected by select ones of the detectors (e.g., select detectors 2-5 and 11-20 of 20 detectors, or select detectors 1 and 6-8 of 20 detectors, or select detectors 9-13 of 20 detectors or some other number of detectors) to probe tissue, such as the epidermis or the dermis where measurement information for the epidermis is substantially independent of measurement information for the dermis, and where measurement information for the dermis is substantially independent of measurement information for the epidermis, or finer gradations of these tissue layers. For example, the relatively shorter wavelengths of visible light between blue and red can be transmitted from the sources and detected by the detectors that are relatively close to the sources (e.g., 100 micrometers or closer to the source) for probing the epidermis.

Relatively longer wavelengths of light (e.g., red, IR, or both) can be transmitted from the sources and detected by the detectors that are relatively far from the sources (e.g., 100 micrometers or farther from the sources) for probing the dermis or deeper, such as buried skin flap used in flap replacement surgery for breast reconstruction, for example. The oximeter probe is adapted for receiving input for the selection of combinations of select wavelengths (e.g., short or long) and select detectors (e.g., close to the sources, such as closer then 100 micrometers, or far from the sources, such as farther than 100 micrometers) where the selected combination are used by the probe for probing different tissue layers of tissue, such as the epidermis or the dermis. The oximeter probe is adapted to make these selections of wavelengths and detectors based on select tissue depths that a user has selected for probing or substantially automatically.

In an implementation, one or more sources can be adapted for emitting wavelengths of light in a first spectral range and not in a second spectral range, or for emitting light in the second spectral range but not the first spectral range where there first and second spectral ranges may not overlap. The first spectral range may include light in the visible range, such as at wavelengths between blue light and red light. The second spectral range may include red light, IR, or both.

Data Weighting Detector Structures. Detector structures 125 that are positioned at increasing distances from source structures 120 receive decreasing amounts of reflectance from tissue. Therefore, the reflectance data generated by detector structures 125 having relatively short source-to-detector distances (e.g., S1-D4 and S2-D8 of FIG. 1B) tends to exhibit intrinsically higher signals compared to reflectance data generated by detector structures having relatively long source-to-detector distances (e.g., S1-D8 and S2-D4 of FIG. 1B). Fit algorithms may therefore preferentially fit the simulated reflectance curves to the reflectance data that is generated by detector structures 125 having relatively short source-to-detectors distances (e.g., source-to-detector distances less than or equal to the average distance between the source structures and the detector structures) more tightly than reflectance data that is generated by detector structures having relatively long source-to-detector distances (e.g., source-to-detector distances greater than the average distance). For relatively accurate determination of the optical properties from the reflectance data, this distance-proportional skew may be undesirable and may be corrected by weighting the reflectance data as described immediately below.

Figure 9:
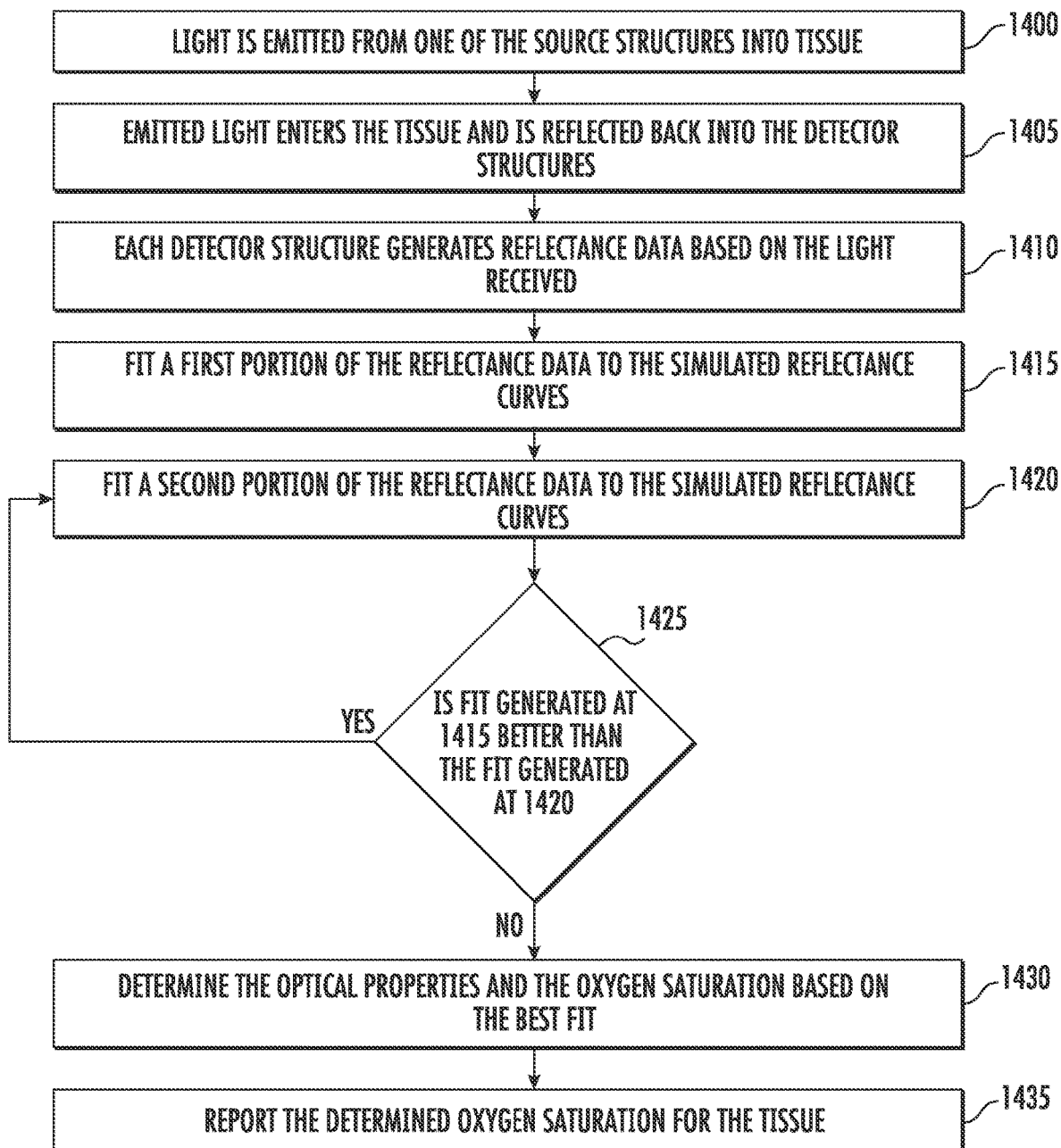
FIG. 9 shows a flow diagram of a method for weighting reflectance data generated by select ones of the detector structures.

FIG. 9 shows a flow diagram of a method for weighting reflectance data generated by select detector structures 125. The flow diagram represents one example implementation. Steps may be added to, removed from, or combined in the flow diagram without deviating from the scope of the implementation.

At 1400, oximeter probe 101 emits light from one of the source structures, such as source structure 120a into tissue. After the emitted light reflects from the tissue, detector structures 125 detect the light, step 1405, and generate reflectance data for the tissue, step 1410. Steps 1400, 1405, and 1410 may be repeated for multiple wavelengths of light and for one or more other source structures, such as source structure 120b. At 1415, oximeter probe 101 fits a first portion of the reflectance data to the simulated reflectance curves 315. The first portion of the reflectance data is generated by a first portion of detector structures that are less than a threshold distance from the source structure. The threshold distance may be the average distances (e.g., approximate mid-range distance) between the source structures and the detector structures. At 1420, reflectance data for a second portion of the reflectance data is fitted to the simulated reflectance curves. The second portion of reflectance data is generated by the first portion of the detector structures and another detector structure that is at the next largest source-to-detector distance from the source compared to the threshold distance. For example, if the first portion of detector structures includes detector structures 125c, 125d, 125e, and 125f, then the detector structure that is at the next largest source-to-detector distance is detector structure 125g (see Table 1).

At 1425, the fit generated at step 1415 is compared to the fit generated at step 1420 to determine whether the fit generated at step 1420 is better than the fit generated at 1415. As will be understood by those of skill in the art, a "closeness" of a fit of data to a curve is quantifiable based on a variety of parameters, and the closeness of fits are directly comparable to determine the data having a closer fit to a curve. As will be further understood, a closer fit is sometimes also referred to as a better fit or a tighter fit. If the fit generated at step 1420 is better than the fit generated at step 1415, then steps 1420 and 1425 are repeated with reflectance data that is generated by detector structures that include an additional detector structure (according to the example being considered, detector structure 125c) that is positioned at a next increased source-to-detector distance from the source. Alternatively, if the fit generated at step 1420 is not better than the fit generated at step 1415, then the reflectance data for detector structures 125 that are positioned at source-to-detector distances that are greater than the threshold distance are not used in the fit. Thereafter, oximeter probe 101 uses the fit generated at 1415 or step 1420 (if better than the fit determined at step 1415) to determine the optical properties and the oxygen saturation of the tissue, step 1430. Thereafter, oxygen saturation is reported by oximeter probe 101, such as on display 115, step 1435.

According to an alternative implementation, if the fit generated at step 1420 is not better than the fit generated at step 1415, then the reflectance data are weighted by a weighting factor for detector structures that have source-to-detector distances that are greater than the threshold distance so that this weighted reflectance data has a decreased influence on the fit. Reflectance data that is not used in a fit may be considered as having a zero weight and may be associated with reflectance from tissue below the tissue layer of interest. Reflectance from tissue below the tissue layer of interest is said to exhibit a characteristic kink in the reflectance curve that indicates this particular reflectance.

It is noted that curve-fitting algorithms that fit the reflectance data to the simulated reflectance curves may take into account the amount of uncertainty of the reflectance data as well as the absolute location of the reflectance data. Uncertainty in the reflectance data corresponds to the amount of noise from the generation of the reflectance data by one of the detector structures, and the amount of noise can scale as the square root of the magnitude of the reflectance data.

According to a further implementation, oximeter probe 101 iteratively weights the reflectance data based on the amount of noise associated with the measurements of the reflectance data. Specifically, the reflectance data generated by detector structures having relatively large source-to-detector distances generally have lower signal-to-noise ratio compared to the reflectance data generated by detector structure having relatively short source-to-detector distances. Weighting the reflectance data generated by detector structures having relatively large source-to-detector distances allows for this data to contribute to the fit substantially equally to other reflectance data.

Stored Simulated Reflectance Curves. According to a specific embodiment, the memory stores a number of Monte Carlo-simulated reflectance curves 315 ("simulated reflectance curves"), which may be generated by a computer for subsequent storage in the memory. Each of the simulated reflectance curves 315 represents a simulation of light (e.g., near infrared light) emitted from one or more simulated light sources into simulated tissue and reflected from the simulated tissue into one or more simulated detectors. Simulated reflectance curves 315 are for a specific configuration of simulated light sources and simulated detectors, such as the configuration of light sources 120 and detectors 125 in tissue oximetry probe 127, or the like. Therefore, simulated reflectance curves 315 model light emitted from, and collected by, tissue oximetry device 100. Further, each of the simulated reflectance curves 315 represents a unique real tissue condition, such as specific tissue absorption and tissue scattering values that relate to particular concentrations of tissue chromophores and densities of tissue scatterers. The number of simulated reflectance curves stored in memory 117 may be relatively large and can represent nearly all, if not all, practical combinations of optical properties and tissue properties that may be present in real tissue that is analyzed for viability by tissue oximetry device 100. While memory 117 is described herein as storing Monte Carlo-simulated reflectance curves, memory 117 may store simulated reflectance curves generated by methods other than Monte Carlo methods, such as using the diffusion approximation.

Figure 10:
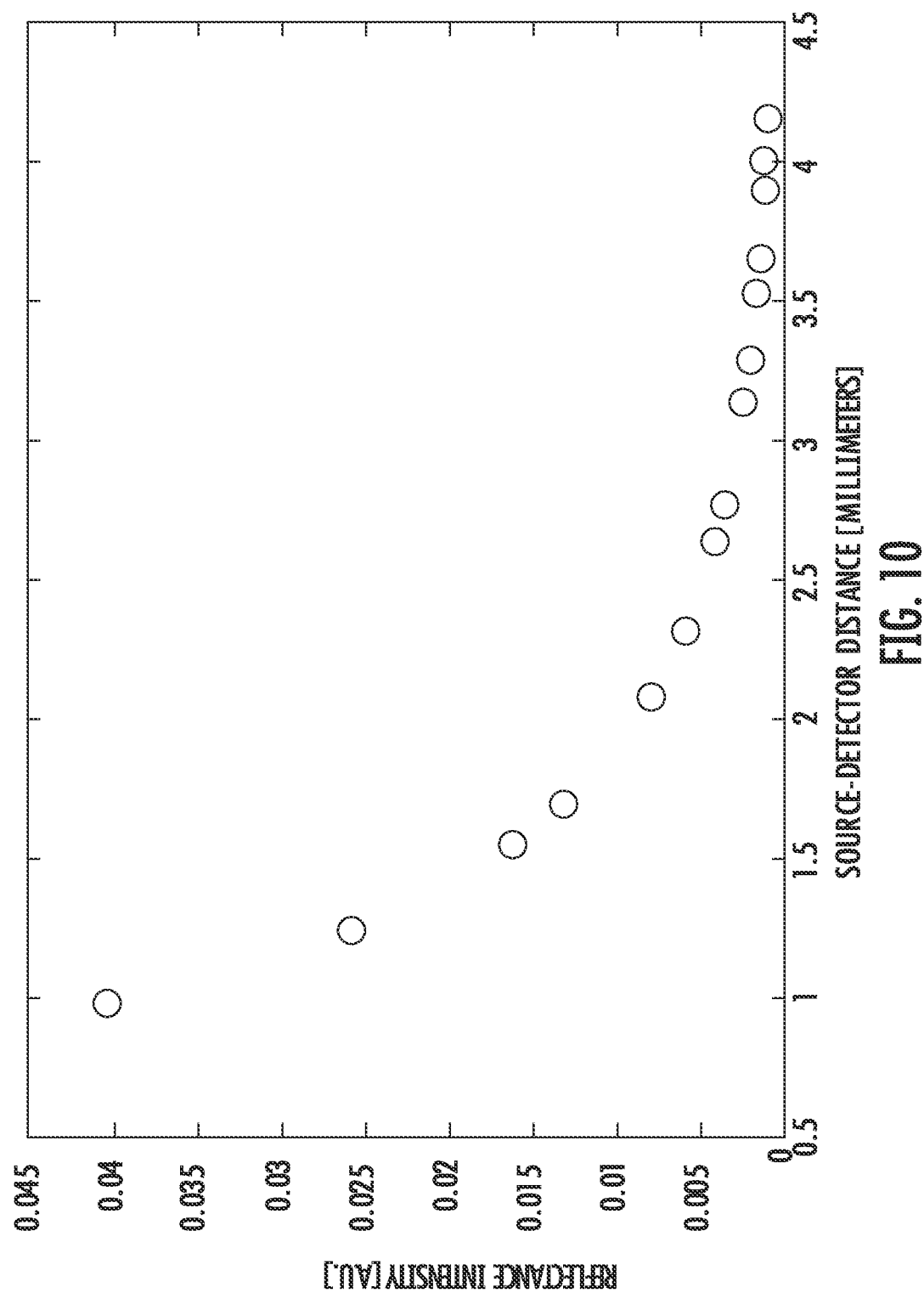
FIG. 10 is an example graph of a number of Monte Carlo-simulated reflectance curves.

FIG. 10 is an example graph of a reflectance curve, which may be for a specific configuration of light sources 120 and detectors 125, such as one of the configurations light sources and detectors of tissue oximetry probe 127, or the like. The horizontal axis of the graph represents the distances between light sources 120 and detectors 125 (i.e., source-detector distances). If the distances between light sources 120 and detectors 125 are appropriately chosen, and the simulated reflectance curve is a simulation for light sources 120 and detectors 125, then the lateral spacings between the data points in the simulated reflectance curve will be relatively uniform. Such relatively uniform spacings can be seen in the simulated reflectance curve in FIG. 4. The vertical axis of the graph represents the simulated reflectance of light that reflects from tissue and is detected by detectors 125. As shown by the simulated reflectance curve, the reflectance that reaches detectors 125 varies with the distance between light sources 120 and detectors 125.

According to one implementation, memory 117 stores a select number of points for each of the simulated reflectance curves 315 and might not store the entirety of the simulated reflectance curves. The number of points stored for each of simulated reflectance curves 315 may match the number of source-detector pairs. For example, if tissue oximetry probe 115 includes two light sources 120a and 120c and includes eight detectors 125a-125h, then tissue oximetry probe 100 includes sixteen source-detector pairs, and memory 117 may thus store sixteen select data points for each of the simulated reflectance curves, where stored data points are for the specific source-detectors distances (i.e., distances between the light sources and the detectors).

Thus, the simulated reflectance curve database stored in memory 117 might be sized 16×3×5850 where sixteen points are stored per curve for three different wavelengths that may be generated and emitted by each light source 210 and where there are a total of 5850 curves spanning the optical property ranges. Alternatively, the simulated reflectance curve database stored in memory 117 might be sized 16×4×5850 where sixteen points are stored per curve for four different wavelengths that may be generated and emitted by each light source and where there are a total of 5850 curves spanning the optical property ranges. The 5850 curves originate, for example, from a matrix of 39 absorption coefficients $\mu_s'$ values and 150 absorption coefficient $\mu_a$ values. The $\mu_s'$ values might range from 5:5:24 centimeter$^{-1}$ ($\mu_s'$ depends on the value for g). The $\mu_a$ values might range from 0.01:0.01:1.5. It will be understood the foregoing described ranges are example ranges and the number source-detectors pairs, the number of wavelengths generated by each light source, and the number of simulated reflectance curves may be smaller or larger.

Figure 11A:
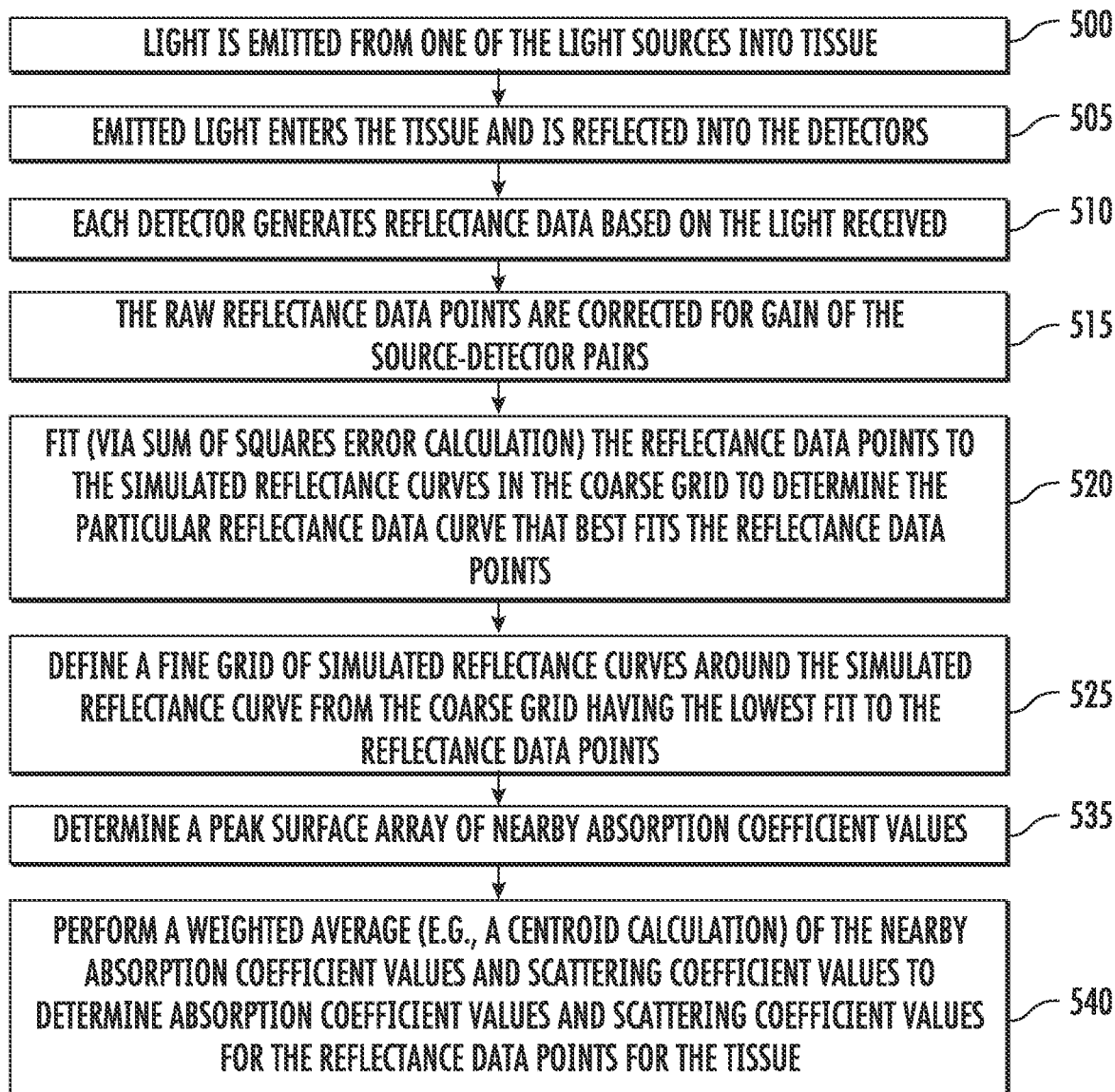
FIG. 11A is a flow diagram of a method for determining the optical properties of tissue (e.g., real tissue) by tissue oximetry device where the tissue oximetry device uses reflectance data and simulated reflectance curves to determine the optical properties.

Tissue Analysis. FIG. 11A is a flow diagram of a method for determining the optical properties of tissue (e.g., real tissue) by tissue oximetry device 100 where the tissue oximetry device uses reflectance data and simulated reflectance curves 315 to determine the optical properties. The optical properties may include the absorption coefficient $\mu_a$ and the scattering coefficients $\mu_s$ of the tissue. A further method for conversion of the absorption coefficient $\mu_a$ and the scattering coefficients of the tissue $\mu_s$ to oxygen saturation values for tissue is described in further detail below. The flow diagram represents one example embodiment. Steps may be added to, removed from, or combined in the flow diagram without deviating from the scope of the embodiment.

At 500, tissue oximetry device 100 emits light (e.g., near infrared light) from one of the light sources 120, such as light source 120a into tissue. The tissue oximetry device is generally in contact with the tissue when the light is emitted from the light source. After the emitted light reflects from the tissue, detectors 125 detect a portion this light, step 505, and generate reflectance data points for the tissue, step 510. Steps 500, 505, and 510 may be repeated for multiple wavelengths of light (e.g., red, near infrared light, or both) and for one or more other light sources, such as light source 120c. The reflectance data points for a single wavelength might include sixteen reflectance data points if, for example, tissue oximetry probe 115 has sixteen source-detectors distances. The reflectance data points are sometimes referred to as an N-vector of the reflectance data points.

At 515, the reflectance data points (e.g., raw reflectance data points) are corrected for gain of the source-detector pairs. During calibration of the source-detector pairs, gain corrections are generated for the source-detector pairs and are stored in memory 117. Generation of the gain corrections are described in further detail below.

At 520, processor 116 fits (e.g., via a sum of squares error calculation) the reflectance data points to the simulated reflectance curves 315 to determine the particular reflectance data curve that best fits (i.e., has the lowest fit error) the reflectance data points. According to one specific implementation, a relatively small set of simulated reflectance curves that are a "coarse" grid of the database of the simulated reflectance curves is selected and utilized for fitting step 520. For example, given 39 scattering coefficient $\mu_s'$ values and 150 absorption coefficient $\mu_a$ values, a coarse grid of simulated reflectance curves might be determined by processor 116 by taking every 5th scattering coefficient $\mu_s'$ value and every 8th absorption coefficients $\mu_a$ for a total of 40 simulated reflectance curves in the coarse grid. It will be understood that the foregoing specific values are for an example embodiment and that coarse grids of other sizes might be utilized by processor 116. The result of fitting the reflectance data points to the coarse grid is a coordinate in the coarse grid $(\mu_a, \mu_s')_{coarse}$ of the best fitting simulated reflectance curve.

At 525, the particular simulated reflectance curve from the coarse grid having the lowest fit error is utilized by processor 116 to define a "fine" grid of simulated reflectance curves where the simulated reflectance curves in the fine grid are around the simulated reflectance curve from the coarse grid having the lowest fit error.

That is, the fine grid is a defined size, with the lowest error simulated reflectance curve from the coarse grid defining the center of the fine grid. The fine grid may have the same number of simulated reflectance curves as the coarse grid or it may have more or fewer simulated reflectance curves. The fine grid is substantially fine so as to provide a sufficient number of points to determine a peak surface array of nearby absorption coefficient $\mu_a$ values and scattering coefficient $\mu_s'$ values, step 530, in the fine grid. Specifically, a threshold may be set by processor 116 utilizing the lowest error value from the coarse grid plus a specified offset. The positions of the scattering coefficient $\mu_s'$ and the absorption coefficient $\mu_a$ on the fine grid that have errors below the threshold may all be identified for use in determining the peak surface array for further determining the scattering coefficient $\mu_s'$ and the absorption coefficient $\mu_a$ for the reflectance data. Specifically, an error fit is made for the peak to determine the absorption coefficient $\mu_a$ and the scattering coefficient $\mu_s'$ values at the peak. A weighted average (e.g., a centroid calculation) of the absorption coefficient $\mu_a$ and the scattering coefficient $\mu_s'$ values at the peak may be utilized by the tissue oximetry device for the determination of the absorption coefficient $\mu_a$ and the scattering coefficient $\mu_s'$ values for the reflectance data points for the tissue, step 540.

Weights for the absorption coefficient $\mu_a$ and the scattering coefficient $\mu_s'$ values for the weighted average may be determined by processor 116 as the threshold minus the fine grid error. Because points on the fine grid are selected with errors below the threshold, this gives positive weights. The weighted calculation of the weighted average (e.g., centroid calculation) renders the predicted scattering coefficient $\mu_s'$ and absorption coefficient $\mu_a$ (i.e., $(\mu_a, \mu_s')_{fine}$) for the reflectance data points for the tissue. Other methods may be utilized by the tissue oximetry device, such as fitting with one or more of a variety of non-linear least squares to determine the true minimum error peak for the scattering coefficient us.

According to one implementation, processor 116 calculates the log of the reflectance data points and the simulated reflectance curves, and divides each log by the square root of the source-detector distances (e.g., in centimeters). These log values divided by the square root of the of the source-detector distances may be utilized by processor 116 for the reflectance data points and the simulated reflectance curves in the foregoing described steps (e.g., steps 515, 520, 525, and 530) to improve the fit of the reflectance data points to the simulated reflectance curves.

According to another implementation, the offset is set essentially to zero, which effectively gives an offset of the difference between the coarse grid minimum and the fine grid minimum. The method described above with respect to FIG. 11A relies on minimum fit error from the coarse grid, so the true minimum error on the fine grid is typically lower. Ideally, the threshold is determined from the lowest error on the fine grid, which would typically require additional computation by the processor.

Figure 11B:
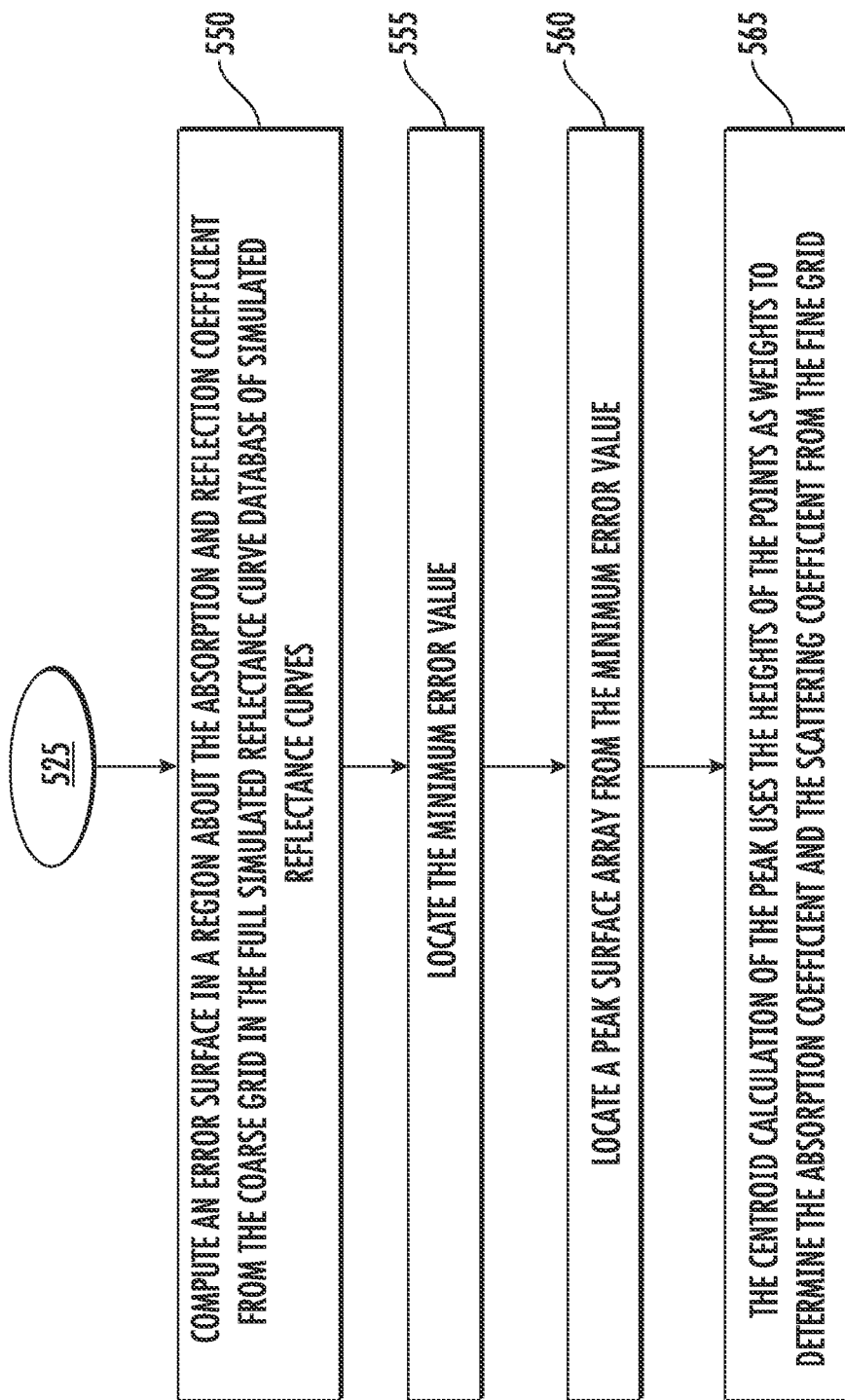
FIG. 11B is a flow diagram of a method for finding the particular simulated reflectance curve that best bits the reflectance data points in the fine grid according to one implementation.

The following is a further detailed description for finding the particular simulated reflectance curve that best fits the reflectance data points in the fine grid according to one implementation. FIG. 11B is a flow diagram of a method for finding the particular simulated reflectance curve that best fits the reflectance data points in the fine grid according to one implementation. The flow diagram represents one example embodiment. Steps may be added to, removed from, or combined in the flow diagram without deviating from the scope of the embodiment.

Subsequent to determining the particular simulated reflectance curve $(\mu_a, \mu_s')_{coarse}$ from the coarse grid that best fits the reflectance data points at step 525, processor 116 computes an error surface in a region about $(\mu_a, \mu_s')_{coarse}$ in the full simulated reflectance curve database (i.e., $16 \times 3 \times 5850$ $(\mu_a, \mu_s')$ database) of simulated reflectance curves, step 550. The error surface is denoted as: $err(\mu_a, \mu_s')$. Thereafter, processor 116 locates the minimum error value in $err(\mu_a, \mu_s')$, which is referred to as $err_{min}$, step 555. Processor 116 then generates a peak surface array from $err(\mu_a, \mu_s')$ that is denoted by $pksurf(\mu_a, \mu_s')=k+err_{min}-err(\mu_a, \mu_s')$ if the peak surface is greater than zero, or $pksurf(\mu_a, \mu_s')=k+err_{min}-err(\mu_a, \mu_s')=0$ if the peak surface is less than or equal to zero, step 560. In the expression k is chosen from a peak at the minimum point of $err(\mu_a, \mu_s')$ with a width above zero of approximately ten elements. The center-of-mass (i.e., the centroid calculation) of the peak in $pksurf(\mu_a, \mu_s')$ uses the heights of the points as weights, step 565. The position of the center-of-mass is the interpolated result for the absorption coefficient $\mu_a$ and the scattering coefficient $\mu_s'$ for the reflectance data points for the tissue The method described above with respect to FIGS. 5A and 5B for determining the absorption coefficient $\mu_a$ and the scattering coefficient $\mu_s'$ for reflectance data points for tissue may be repeated for each of the wavelengths (e.g., 3 or 4 wavelengths) generated by each of light sources 120.

Oxygen Saturation Determination. According to a first implementation, processor 116 determines the oxygen saturation for tissue that is probed by tissue oximetry device 100 by utilizing the absorption coefficients $\mu_a$ (e.g., 3 or 4 absorption coefficients $\mu_a$) that are determined (as described above) for the 3 or 4 wavelengths of light that are generated by each light source 120. According to a first implementation, a look-up table of oxygen saturation values is generated for finding the best fit of the absorption coefficients $\mu_a$ to the oxygen saturation. The look-up table may be generated by assuming a range of likely total hemoglobin, melanin, and oxygen saturation values and calculating $\mu_a$ for each of these scenarios. Then, the absorption coefficient $\mu_a$ points are converted to a unit vector by dividing by a norm of the unit vector to reduce systematic error and only depend on relative shape of curve. Then the unit vector is compared to the look-up table to find the best fit, which gives the oxygen saturation.

According to a second implementation, processor 116 determines the oxygen saturation for the tissue by calculating the net analyte signal (NAS) of deoxygenated hemoglobin and oxygenated hemoglobin. The NAS is defined as the portion of the spectrum that is orthogonal to the other spectral components in the system. For example, the NAS of deoxygenated hemoglobin is the portion of the spectrum that is orthogonal to oxygenated hemoglobin spectrum and melanin spectrum. The concentrations of deoxygenated and oxygenated hemoglobin can then be calculated by vector multiplying the respective NAS and dividing by a norm of the NAS squared. Oxygen saturation is then readily calculated as the concentration of oxygenated hemoglobin divided by the sum of oxygenated hemoglobin and deoxygenated hemoglobin. Anal. Chem. 58:1167-1172 (1986) by Lorber is incorporated by reference herein and provides a framework for a further detailed understanding of the second implementation for determining the oxygen saturation for the tissue.

According to one embodiment of tissue oximetry device 100, the reflectance data is generated by detectors 125 at 30 Hertz, and oxygen saturation values are calculated at approximately 3 Hertz. A running average of determined oxygen saturation values (e.g., at least three oxygen saturation values) may be displayed on display 112, which might have an update rate of 1 Hertz.

Optical Properties. As described briefly above, each simulated reflectance curve 315 that is stored in memory 117 represents unique optical properties of tissue. More specifically, the unique shapes of the simulated reflectance curves, for a given wavelength, represent unique values of the optical properties of tissue, namely the scattering coefficient $(\mu_s)$, the absorption coefficient $(\mu_a)$, the anisotropy of the tissue (g), and index of refraction of the tissue from which the tissue properties may be determined.

The reflectance detected by detectors 125 for relatively small source-to-detector distances is primarily dependent on the reduced scattering coefficient, $\mu_s'$. The reduced scattering coefficient is a "lumped" property that incorporates the scattering coefficient $\mu_s$ and the anisotropy g of the tissue where $\mu_s'=\mu_s(1-g)$, and is used to describe the diffusion of photons in a random walk of many steps of size of $1/\mu_s'$ where each step involves isotropic scattering. Such a description is equivalent to a description of photon movement using many small steps $1/\mu_s$ which each involve only a partial deflection angle if there are many scattering events before an absorption event, i.e., $\mu_a \ll \mu_s'$.

In contrast, the reflectance that is detected by detectors 125 for relatively large source-detector distances is primarily dependent on the effective absorption coefficient $\mu_{\mathit{eff}}$ which is defined as $\sqrt{3\mu_a(\mu_a+\mu_s')}$, which is a function of both $\mu_a$ and $\mu_s'$.

Thus, by measuring reflectance at relatively small source-detector distances (e.g., D1 between light source 120a and detector 125e and D9 between light source 120c and detector 125a) and relatively large source-detector distances (e.g., D5 between light source 120a and detector 125a and D10 between light source 120c and detector 125e), both $\mu_a$ and $\mu_s'$ can be independently determined from one another. The optical properties of the tissue can in turn provide sufficient information for the calculation of oxygenated hemoglobin and deoxygenated hemoglobin concentrations and hence the oxygen saturation of the tissue.

Figure 12:
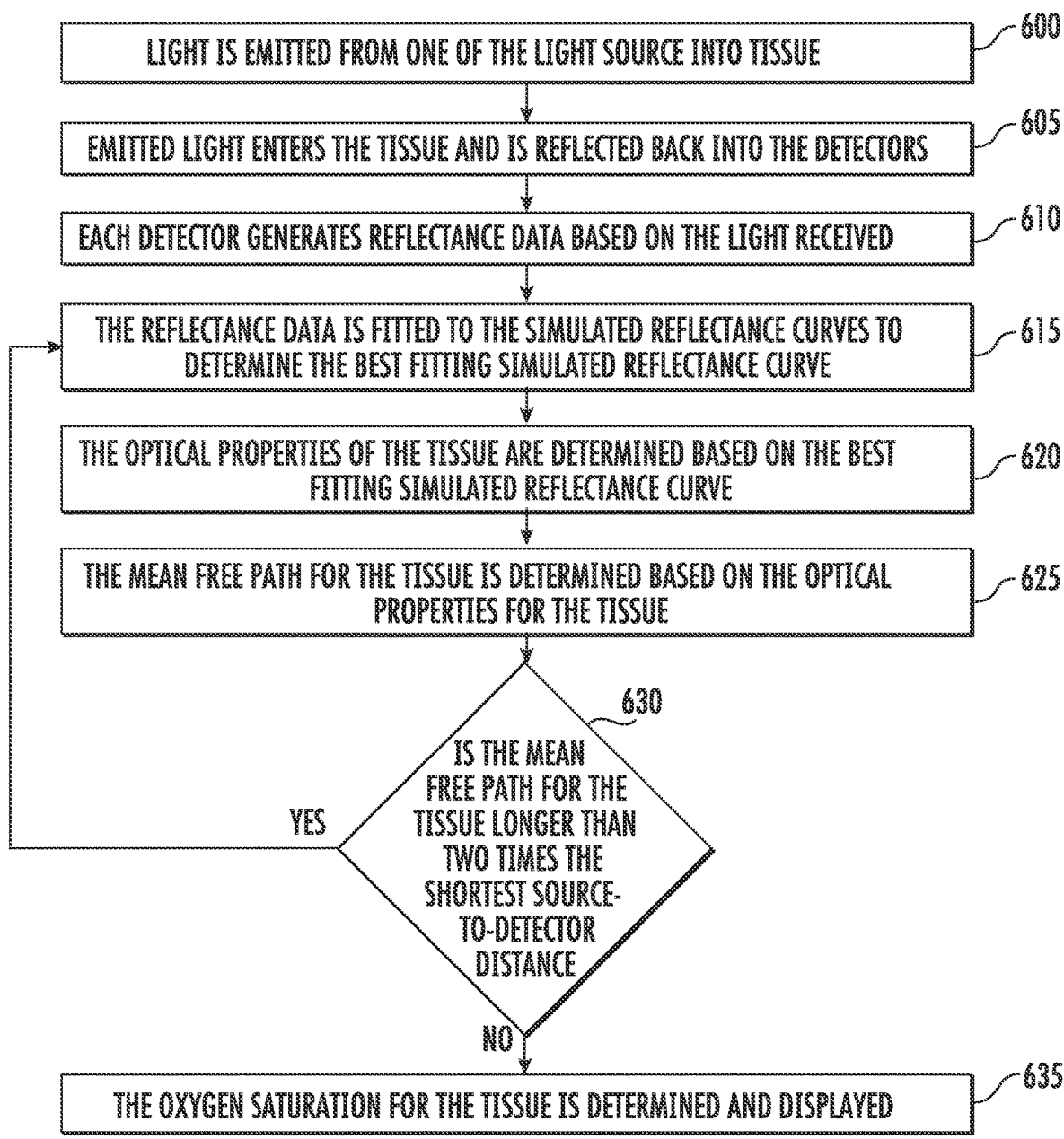
FIG. 12 is a flow diagram of another method for determining the optical properties and tissue properties of real tissue by the tissue oximetry device.

Iterative Fit for Data Collection Optimization. FIG. 12 is a flow diagram of another method for determining the optical properties of tissue by tissue oximetry device 100. The flow diagram represents one example embodiment. Steps may be added to, removed from, or combined in the flow diagram without deviating from the scope of the embodiment.

At 600, tissue oximetry device 100 emits light (e.g., near infrared light) from one of the light sources, such as light source 120a into tissue. After the emitted light reflects from the tissue, detectors 125 detect the light, step 605, and generate reflectance data for the tissue, step 610. Steps 600, 605, and 610 may be repeated for multiple wavelengths of light and for one or more other light sources, such as light source 120c. At 615, tissue oximetry device 100 fits the reflectance data to simulated reflectance curves 315 and determines the simulated reflectance curve to which the reflectance data has the best fit. Thereafter, tissue oximetry device 100 determines the optical properties (e.g., $\mu_a$, and $\mu_s'$) for the tissue based on the optical properties of the simulated reflectance curve that best fits the reflectance data, step 620.

At 625 tissue oximetry device 100 determines the mean free path of the light in the tissue from the optical properties (e.g., mfp=$1/(\mu_a+\mu_s')$) determined at step 620. Specifically, the mean free path can be determined from the optical properties obtained from a cumulative reflectance curve that includes the reflectance data for all of the source-detector pairs (e.g., pair 1: light source 120a-detector 125e; pair 2: light source 120a-detector 125f; pair 3: light source 120a-detector 125g; pair 4: light source 120a-detector 125h; pair 5: light source 120a-detector 125a; pair 6: light source 120a-detector 125b; pair 7: light source 120a-detector 125c; pair 8: light source 120a-detector 125d; . . . pair 9: light source 120c-detector 125e, pair 10: light source 120b-detector 125f . . . and others.).

At 630, tissue oximetry device 100 determines whether the mean free path calculated for a given region of the tissue is longer than two times the shortest source-to-detector distance (e.g., D1 between light source 120a and detector 125e, and D9 between light source 120c and detector 125a). If the mean free path is longer than two times the shortest source-to-detector distance, then the collected reflectance data is re-fitted to the simulated reflectance curves (i.e., reanalyzed) without utilizing the reflectance data collected from the detectors for the source-to-detector pairs (e.g., pair 1: light source 120a-detector 125e and pair 9 light source 120c-detector 125a) having the shortest source-to-detector distance. For example, steps 615-630 are repeated without use of the reflectance data from detector 125e with light source 120a acting as the source for detector 125e, and without use of the reflectance data from detector 125a with light source 120c acting as the source for detector 125a. The process of calculating the mean free path and discarding the reflectance data for one or more source-detector pairs may be repeated until no source-detector pairs that contribute reflectance data to the fit have a source-to-detector distance shorter than one half of the calculated mean free path. Thereafter, oxygen saturation is determined from the best fitting simulated reflectance curve and reported by tissue oximetry device 110, such as on display 112, step 635.

Light that is emitted from one of the light sources 120 into tissue and that travels less than half of the mean free path is substantially non-diffusely reflected. The re-emission distance for this light is strongly dependent on the tissue phase function and the local tissue composition. Therefore, using the reflectance data for this light tends to result in a less accurate determination of the optical properties and tissue properties as compared with the reflectance data for light that has undergone multiple scattering events.

Data Weighting. Detectors 125 that are positioned at increasing distances from light sources 120 receive decreasing amounts of reflectance from tissue. Therefore, the reflectance data generated by detectors 125 having relatively short source-to-detector distances (e.g., D1) tends to exhibit intrinsically lower noise compared to reflectance data generated by detectors having relatively long source-to-detector distances (e.g., D5 and D10). Fit algorithms may therefore preferentially fit the simulated reflectance curves to the reflectance data that is generated by detectors 125 having relatively short source-to-detectors distances (e.g., source-to-detector distances less than or equal to the average distance between the light sources and the detectors) more tightly than reflectance data that is generated by detectors having relatively long source-to-detector distances (e.g., source-to-detector distances greater than the average distance). For relatively accurate determination of the optical properties from the reflectance data, this distance-proportional skew may be undesirable and may be corrected by weighting the reflectance data as described immediately below.

Figure 13:
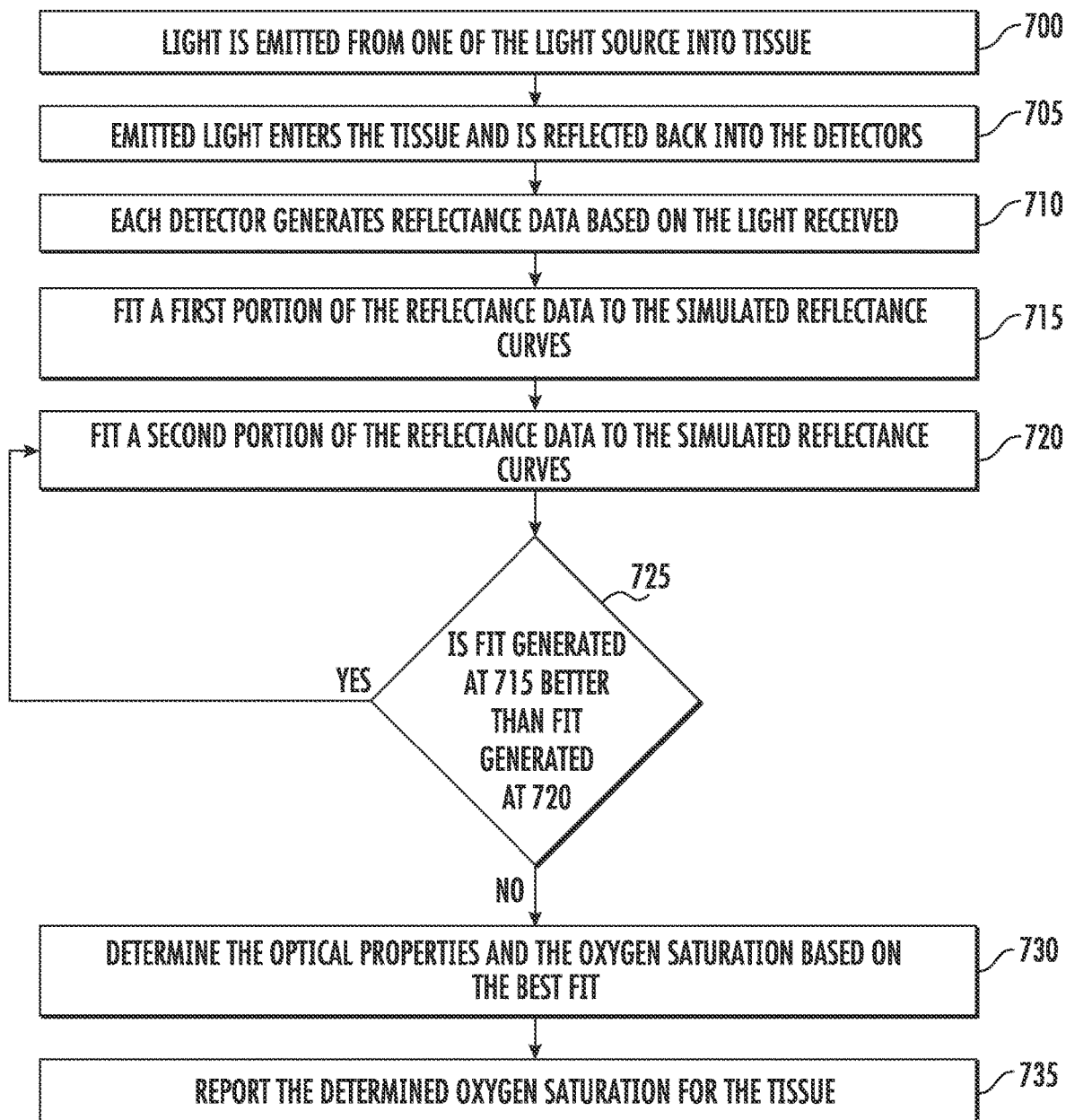
FIG. 13 is a flow diagram of a method for weighting reflectance data generated by select detectors.

FIG. 13 is a flow diagram of a method for weighting reflectance data generated by select detectors 125. The flow diagram represents one example embodiment. Steps may be added to, removed from, or combined in the flow diagram without deviating from the scope of the embodiment.

At 700, tissue oximetry device 100 emits light from one of the light sources, such as light source 120a into tissue. After the emitted light reflects from the tissue, detectors 125 detect the light, step 705, and generate reflectance data for the tissue, step 710. Steps 700, 705, and 710 may be repeated for multiple wavelengths of light and for one or more other light sources, such as light source 120c. At 715, tissue oximetry device 100 fits a first portion of the reflectance data to the simulated reflectance curves. The first portion of the reflectance data is generated by a first portion of detectors that are less than a threshold distance from the light source. The threshold distance may be the average distances (e.g., approximate mid-range distance) between the light sources and the detectors. At 720, reflectance data for a second portion of the reflectance data is fitted to the simulated reflectance curves. The second portion of reflectance data is generated by the first portion of the detectors and another detector that is at the next largest source-to-detector distance from the source compared to the threshold distance. For example, if the first portion of detectors includes detectors 125c, 125d, 125e, and 125f, then the detector that is at the next largest source-to-detector distance is detector 125g (e.g., closer to light source 120a than detector 125c, see FIGS. 2A and 2B).

At 725, the fit generated at step 715 is compared to the fit generated at step 720 to determine whether the fit generated at step 720 is better than the fit generated at 715. As will be understood by those of skill in the art, a "closeness" of a fit of data to a curve is quantifiable based on a variety of parameters, and the closeness of fits are directly comparable to determine the data having a closer fit (closer fit) to a curve. As will be further understood, a closer fit is sometimes also referred to as a better fit or a tighter fit. If the fit generated at step 720 is better than the fit generated at step 715, then steps 720 and 725 are repeated with reflectance data that is generated by detectors that include an additional detector (according to the example being considered, detector 125c) that is positioned at a next increased source-to-detector distance from the source. Alternatively, if the fit generated at step 720 is not better than the fit generated at step 715, then the reflectance data for detectors 125 that are positioned at source-to-detector distances that are greater than the threshold distance are not used in the fit. Thereafter, tissue oximetry device 100 uses the fit generated at 715 or step 720 (if better than the fit determined at step 715) to determine the optical properties and the oxygen saturation of the tissue, step 730. Thereafter, oxygen saturation is reported by tissue oximetry device 110, such as on display 112, step 735.

According to an alternative embodiment, if the fit generated at step 720 is not better than the fit generated at step 715, then the reflectance data are weighted by a weighting factor for detectors that have source-to-detector distances that are greater than the threshold distance so that this weighted reflectance data has a decreased influence on the fit. Reflectance data that is not used in a fit may be considered as having a zero weight and may be associated with reflectance from tissue below the tissue layer of interest. Reflectance from tissue below the tissue layer of interest is said to exhibit a characteristic kink in the reflectance curve that indicates this particular reflectance.

It is noted that curve-fitting algorithms that fit the reflectance data to the simulated reflectance curves may take into account the amount of uncertainty of the reflectance data as well as the absolute location of the reflectance data. Uncertainty in the reflectance data corresponds to the amount of noise from the generation of the reflectance data by one of the detectors, and the amount of noise can scale as the square root of the magnitude of the reflectance data.

According to a further embodiment, tissue oximetry device 100 iteratively weights the reflectance data based on the amount of noise associated with the measurements of the reflectance data. Specifically, the reflectance data generated by detectors having relatively large source-to-detector distances generally have greater a greater signal-to-noise ratio compared to the reflectance data generated by detector having relatively short source-to-detector distances. Weighting the reflectance data generated by detectors having relatively large source-to-detector distances allows for this data to contribute to the fit substantially equally to other reflectance data.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. Elements of the various described implementations can be combined in any combination. The scope of the invention is defined by the following claims.

The invention claimed is:

1. A method comprising:
using an oximeter to determine an oxygen saturation of a tissue to be measured, wherein the oximeter comprises a processor, memory, display, power source, and probe tip comprising a first source structure and a plurality of detector structures, the processor is coupled to the memory and display, and the power source is coupled to the processor, memory, and display;
emitting first light by the first source structure into the tissue to be measured and detecting a reflection of the first light from the tissue by the detector structures that are closer to the source structure than a threshold distance;
fitting first detector responses, generated by the detector structures that are closer to the source structure than the threshold distance based on the detected first light, to a plurality of simulated reflectance curves stored in the memory;
determining first measurement information for first tissue of the tissue to be measured based on one or more best fitting ones of the simulated reflectance curve to the first detector responses;
emitting second light by the first source structure into the tissue and detecting a reflection of the second light from the tissue by the detector structures that are farther from the source structure than the threshold distance;
fitting second detector responses, that are generated by the detector structures that are farther from the source structure than the threshold distance based on the detected second light, to the plurality of simulated reflectance curves stored in the memory;
determining second measurement information based on one or more best fitting ones of the simulated reflectance curve to the second detector responses;
determining second measurement information for second tissue of the tissue to be measured based on the second light detected by the detector structures that are farther from the source structure than the threshold distance;
based on the first measurement information, calculating and displaying on the display a first oxygen saturation measurement for a first tissue region below a surface of the tissue at a first depth;
based on the second measurement information, calculating and displaying on the display a second oxygen saturation measurement for a second tissue region below the surface of the tissue at a second depth; and
based on the first measurement information and the second measurement information, calculating and displaying on the display a third oxygen saturation measurement for a third tissue region below the surface of the tissue at a combination of the first and second depths, wherein the first tissue is a first depth below the surface of the tissue to be measured, the second tissue is a second depth below the surface of the tissue to be measured, and the first depth is less than the second depth.

2. The method of claim 1 wherein the oximeter is a handheld device, and the power source is a battery.

3. The method of claim 1 wherein the first measurement information is first oximetry information and the second information is second oximetry information.

4. The method of claim 1 comprising:
coupling a multiplexer circuit between the processor and the detector structures.

5. The method of claim 1 comprising:
allowing a user to select a tissue depth of the tissue to be measured for determining the first, second, or third oxygen saturation.

6. The method of claim 1 wherein the determining second measurement information comprises performing a sum of squares error calculation to determine a specific simulated reflectance curve that has the lowest fit error.

7. A method comprising:
providing an oximeter to determine an oxygen saturation of a tissue to be measured, wherein the oximeter comprises a processor, memory, display, power source, and probe tip comprising a first source structure and a plurality of detector structures, the processor is coupled to the memory and display, and the power source is coupled to the processor, memory, and display;
before using the oximeter to make a determination of oxygen saturation, inserting and enclosing the oximeter into a probe cover, wherein the probe comprises
a first portion of the probe cover, wherein the first portion comprises a first open end and a first closed end, opposite to the first open end, and the first closed end comprises a display viewer panel, and
a second portion of the probe cover, wherein the second portion comprises a second open end and a second closed end, opposite to the second open end, the second closed end comprises an optical sensor panel, and coupling of the first open end to the second open end forms a sealed probe cover enclosure for the oximeter device;
while the oximeter is enclosed in the probe cover, emitting first light by the first source structure into the tissue to be measured and detecting a reflection of the first light from the tissue by the detector structures that are closer to the source structure than a threshold distance;
fitting first detector responses, generated by the detector structures that are closer to the source structure than the threshold distance based on the detected first light, to a plurality of simulated reflectance curves stored in the memory;
determining first measurement information for first tissue of the tissue to be measured based on one or more best fitting ones of the simulated reflectance curve to the first detector responses;
while the oximeter is enclosed in the probe cover, emitting second light by the first source structure into the tissue and detecting a reflection of the second light from the tissue by the detector structures that are farther from the source structure than the threshold distance;
fitting second detector responses, that are generated by the detector structures that are farther from the source structure than the threshold distance based on the detected second light, to the plurality of simulated reflectance curves stored in the memory;
determining second measurement information based on one or more best fitting ones of the simulated reflectance curve to the second detector responses;
determining second measurement information for second tissue of the tissue to be measured based on the second light detected by the detector structures that are farther from the source structure than the threshold distance;
based on the first measurement information, calculating and displaying on the display a first oxygen saturation measurement for a first tissue region below a surface of the tissue at a first depth;
based on the second measurement information, calculating and displaying on the display a second oxygen saturation measurement for a second tissue region below the surface of the tissue at a second depth; and
based on the first measurement information and the second measurement information, calculating and displaying on the display a third oxygen saturation measurement for a third tissue region below the surface of the tissue at a combination of the first and second depths, wherein the first tissue is a first depth below the surface of the tissue to be measured, the second tissue is a second depth below the surface of the tissue to be measured, and the first depth is less than the second depth.

8. The method of claim 7 wherein when the oximeter is in the sealed probe cover, a display of the oximeter device is visible through the display viewer panel of the probe cover, light emitted by the oximeter device is transmitted through the optical sensor panel of the probe cover, and light received by the oximeter device is transmitted through the optical sensor panel of the probe cover,
whereby the sealed probe cover enclosure prevents contaminants from outside of the enclosure from contacting the oximeter device contained within an interior of the enclosure, and
the second portion of the probe cover comprises a barrier at the second closed end, the barrier is coupled to the optical sensor panel, and the barrier prevents contaminants on the tissue being measured from contacting the oximeter contained within the interior of the enclosure.

9. The method of claim 7 wherein the oximeter is a handheld device, and the power source is a battery.

10. The method of claim 7 wherein the first measurement information is first oximetry information and the second information is second oximetry information.

11. The method of claim 7 comprising:
coupling a multiplexer circuit between the processor and the detector structures.

12. The method of claim 11 comprising:
coupling a multiplexer circuit to the processor; and
using the multiplexer circuit to route signals to the processor from the detector structures that are closer to the source structure than the threshold distance.

13. The method of claim 12 comprising:
using the multiplexer circuit to not route signals to the processor from the detector structures that are farther from the source structure than the threshold distance.

* * * * *